US006610072B1

(12) United States Patent
Christy et al.

(10) Patent No.: US 6,610,072 B1
(45) Date of Patent: Aug. 26, 2003

(54) SURGICAL LOOP DELIVERY DEVICE

(75) Inventors: William J. Christy, Stonehurst-Oviedo, FL (US); James R. Christy, Sarasota, FL (US); Warren P. Williamson, IV, Loveland, OH (US); Craig Berky, Milford, OH (US)

(73) Assignee: ESD Medical, L.L.C., Winter Park, FL (US)

( * ) Notice: Subject to any disclaimer, the term of this patent is extended or adjusted under 35 U.S.C. 154(b) by 0 days.

(21) Appl. No.: 09/722,875

(22) Filed: Nov. 27, 2000

Related U.S. Application Data

(63) Continuation of application No. 09/241,394, filed on Feb. 2, 1999, now Pat. No. 6,152,936, which is a continuation-in-part of application No. 09/071,811, filed on May 5, 1998, now Pat. No. 5,873,876, which is a continuation of application No. 08/717,990, filed on Sep. 23, 1996, now Pat. No. 5,766,217.

(51) Int. Cl.[7] .............................................. A61B 17/04
(52) U.S. Cl. ....................................... 606/148; 606/144
(58) Field of Search ................................ 606/144, 148

(56) References Cited

U.S. PATENT DOCUMENTS

| | | |
|---|---|---|
| 1,400,653 A | 12/1921 | Barbour |
| 1,461,864 A | 7/1923 | Day |
| 1,625,602 A | 4/1927 | Gould et al. |
| 1,995,196 A | 3/1935 | Wolf ............................ 128/7 |
| 2,227,270 A | 12/1940 | Moore ........................ 128/320 |
| 2,455,833 A | 12/1948 | Trombetta |
| 2,610,631 A | 9/1952 | Calicchio |
| 2,942,604 A | 6/1960 | Gravlee, Jr. |

(List continued on next page.)

OTHER PUBLICATIONS

Jerome S. Seiler, *The Evolution of Tubal Sterilization*, Obstetrical and Gynecological Survey, vol. 39, No. 4, 1984, 9 pgs.

Joan F. Spitaleri, M.D., *A Second Look at the Pomeroy Method of Tubal Sterilization*, New York State Journal of Medicine, Apr., 1984, 3 pgs.

Melvin R. Cohen, M.D. et al., *Pomeroy Tubal Sterilization via Laparoscopy*, vol. 18, No. 6, Jun. 1977, 1 pg.

Jordan Phillips et al., *The Evolution of Laparoscopic Sterilization*, Int. J Gynecol Obstet 14:59–64, 1976, 6 pgs.

Per E. Bordahl, M.D., *Tubal Sterilization: A Historical Review*, The Journal of Reproductive Medicine, vol. 30, No. 1, Jan. 1985, 9 pgs.

Herbert B. Peterson et al., *The Risk of Pregnancy After Tubal Sterilization: Findings from the U.S. Collaborative Review of Sterilization*, Am J Obstet Gynecol. Apr. 1996, 11 pgs.

James H. Dorsey et al., *Tubal Sterilization by Minilaparotomy and Laparoscopy*, Article, 7 pgs. undated.

Hans A. Hirsch et al., *Changing Methods of Sterilization as Influenced by Laparoscopy*, The Journal of Reproductive Medicine, vol. 16, No. 6, Jun. 1976, 6 pgs.

Clifford R. Wheeless et al., *Laparoscopy and Tubal Sterilization*, Operations for Non–neoplastic Conditions, Chapter 17, 16 pgs. undated.

(List continued on next page.)

*Primary Examiner*—Gary Jackson
(74) *Attorney, Agent, or Firm*—Wood, Herron & Evans, L.L.P.

(57) ABSTRACT

A surgical loop delivery device is disclosed in parent disclosures Ser. No. 09/071,811 and U.S. Pat. No. 5,766,217. This device is improved to permit tissue targets larger than the device to be ligated while also maintaining a clear sight path between the surgeon and the target. The surgical loop is also stable during the procedure.

9 Claims, 29 Drawing Sheets

U.S. PATENT DOCUMENTS

| | | | |
|---|---|---|---|
| 3,033,204 A | 5/1962 | Wood | 128/326 |
| 3,040,747 A | 6/1962 | Wood | |
| 3,476,114 A | 11/1969 | Shannon et al. | 128/326 |
| 3,476,115 A | 11/1969 | Graeff et al. | |
| 3,760,810 A | 9/1973 | Van Hoorn | |
| 3,802,074 A | 4/1974 | Hoppe | 30/134 |
| 3,820,544 A | 6/1974 | Semm | |
| 3,934,589 A | 1/1976 | Zimmer | |
| 3,967,625 A | 7/1976 | Yoon | 128/326 |
| 3,985,138 A | 10/1976 | Jarvik | 128/326 |
| 4,018,229 A | 4/1977 | Komiya | 128/326 |
| 4,069,825 A | 1/1978 | Akiyama | 128/335.5 |
| 4,146,019 A | 3/1979 | Bass et al. | 128/6 |
| 4,226,239 A | 10/1980 | Polk et al. | 128/303 |
| 4,374,523 A | 2/1983 | Yoon | 128/326 |
| 4,718,419 A | 1/1988 | Okada | 128/303.15 |
| 5,181,919 A | 1/1993 | Bergman et al. | 606/144 |
| 5,217,471 A | 6/1993 | Burkhart | 606/148 |
| 5,226,908 A | 7/1993 | Yoon | 606/141 |
| 5,242,459 A | 9/1993 | Buelna | 606/148 |
| 5,259,366 A | 11/1993 | Reydel et al. | 128/4 |
| 5,281,238 A | 1/1994 | Chin et al. | 606/148 |
| 5,290,284 A | 3/1994 | Adair | 606/37 |
| 5,318,578 A | 6/1994 | Hasson | 606/139 |
| 5,320,629 A | 6/1994 | Noda et al. | 606/139 |
| 5,330,491 A | 7/1994 | Walker et al. | 606/148 |
| 5,334,199 A | 8/1994 | Yoon | 606/144 |
| 5,336,231 A | 8/1994 | Adair | 606/148 |
| 5,373,840 A | 12/1994 | Knighton | 128/4 |
| 5,391,176 A | 2/1995 | De La Torre | 606/148 |
| 5,405,351 A | 4/1995 | Kinet et al. | 606/139 |
| 5,423,837 A | 6/1995 | Mericle et al. | 606/148 |
| 5,454,820 A | 10/1995 | Kammerer et al. | 606/148 |
| 5,486,186 A | 1/1996 | Yoon | 606/148 |
| 5,489,288 A | 2/1996 | Buelna | 606/148 |
| 5,571,120 A | 11/1996 | Yoon | 606/148 |
| 5,643,293 A | 7/1997 | Kogasaka et al. | 606/148 |
| 5,766,216 A | 6/1998 | Gangal et al. | 606/140 |
| 5,766,217 A | 6/1998 | Christy | 606/148 |
| 5,817,111 A | 10/1998 | Riza | 606/148 |
| 5,908,429 A | 6/1999 | Yoon | 606/144 |
| 5,908,435 A | 6/1999 | Samuels | 606/200 |
| 5,921,993 A | 7/1999 | Yoon | 606/140 |
| 5,922,002 A | 7/1999 | Yoon | 606/170 |
| 5,972,002 A | 10/1999 | Bark et al. | 606/140 |
| 5,976,158 A | 11/1999 | Adams | 606/140 |
| 5,992,002 A | 11/1999 | Hung | 29/566.4 |
| 6,152,936 A | 11/2000 | Christy et al. | 606/148 |

OTHER PUBLICATIONS

Richard M. Soderstrom et al., *The Snare Method of Laparoscopic Sterilization: An Analysis of 1,000 Cases with 4 Failures*, The Journal of Reproductive Medicine, vol. 18, No. 5, May 1977, 5 pgs.

SF Palter et al., *A New Device for Laparoscopic Pomeroy Tubal Ligation: the "Endosquid"*, Article, undated, 18 pgs., presented at AAGL in Nov., 2000.

K. Semm, *Tissue–Puncher and Loop–Ligation—New Aids for Surgical–Therapeutic Pelviscopy (Laparoscopy)=Endoscopic Intraabdominal Surgery*, Department of Obstetrics and Gynecology of the University of Kiel and Midwifery School, 1978, 6 pgs.

K. Semm, *Endoscopic Appendectomy*, Department of Obstetrics and Gynecology and Michaelis Midwifery School of the University of Kiel, 1983, 6 pgs.

K.C. Leong, M.D., *Tubal Sterilization*, The Journal of the Maine Medical Association, Mar. 1978, 6 pgs.

Younan Nowzaradan et al., *Laparoscopic Management of Enlarged Cystic Duct*, Surgical Laparoscopy & Endoscopy, vol. 2, No. 4, 1992, 4 pgs.

Jean E. Murray, MD et al., *A Technique for Laparoscopic Pomeroy Tubal Ligation with Endoloop Sutures*, Article, The American College of Obstetricians and Gynecologists, vol. 80, No. 6, Dec. 1992.

Albert George Thomas, M.D. et al., *Laparoscopic Pomeroy Tubal Ligation in a Residency Training Program*, Article, The Journal of the American Association of Gynecologic Laparoscopists, Aug. 1994, vol. 1, No. 4, Part 1.

Michael D. Fox, M.D. et al., *Laparoscopic Pomeroy Tubal Ligation as a Teaching Model for Residents*, Article, The Journal of Reproductive Medicine, Inc., vol. 39, No. 11/Nov. 1994.

C.E. Taner et al., *Pomeroy tubal ligation by laparoscopy and minilaparotomy*, Article, Advances in Contraception, 1994; 10:151–155.

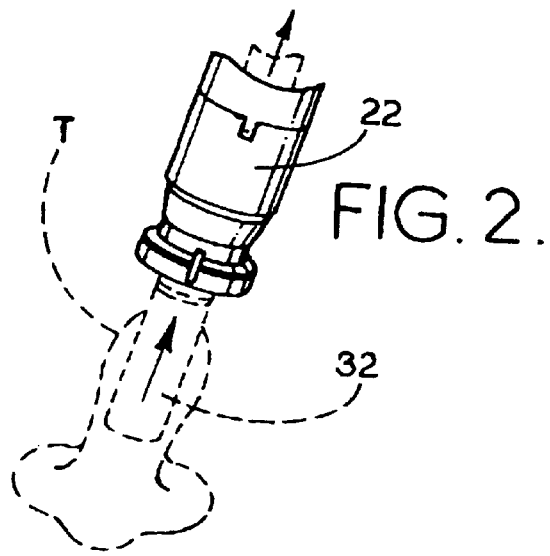
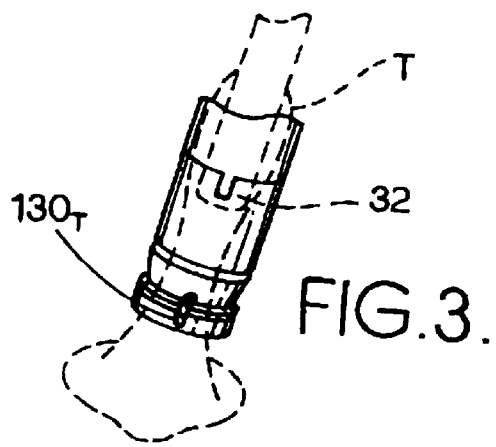
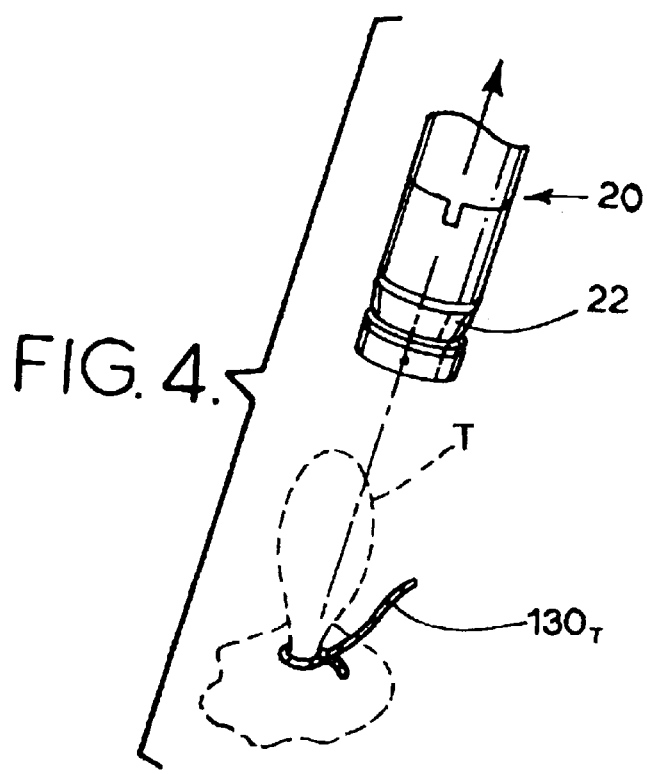

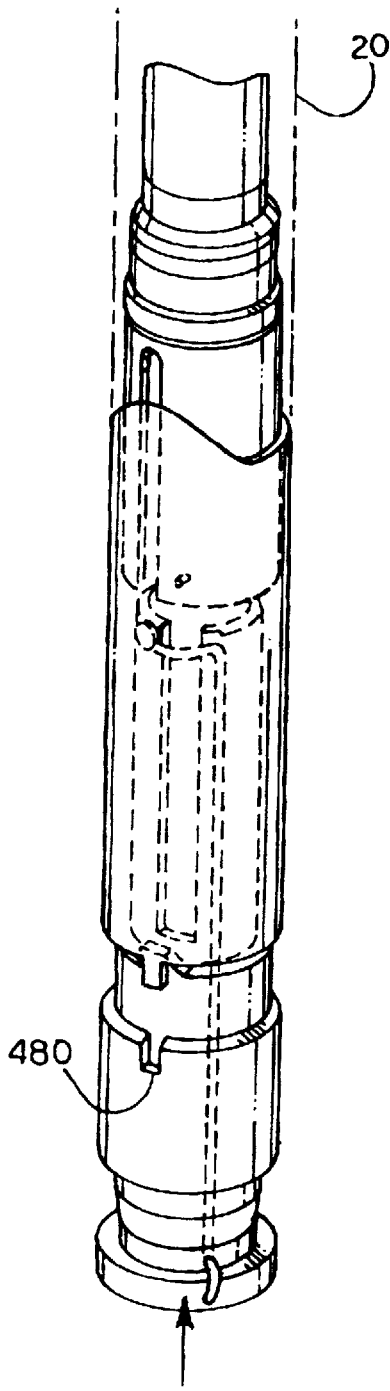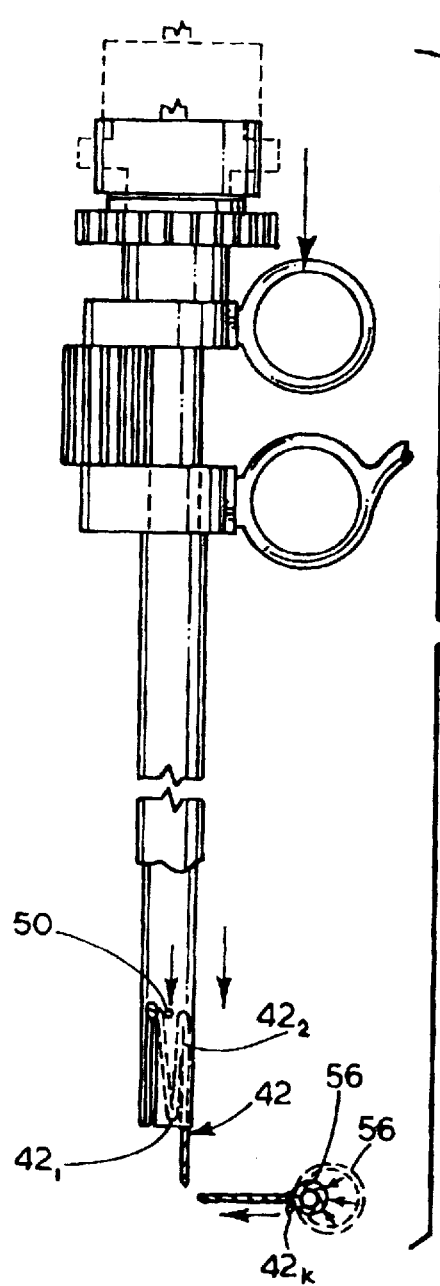
FIG. 6.
FIG. 7.

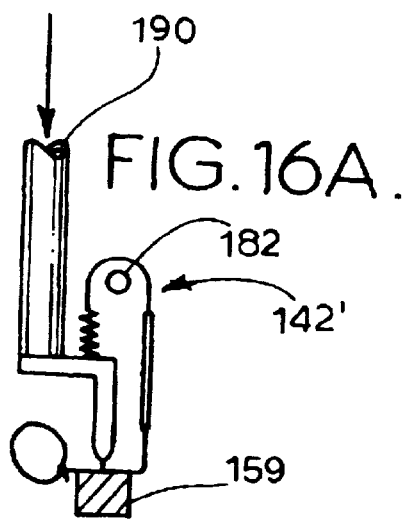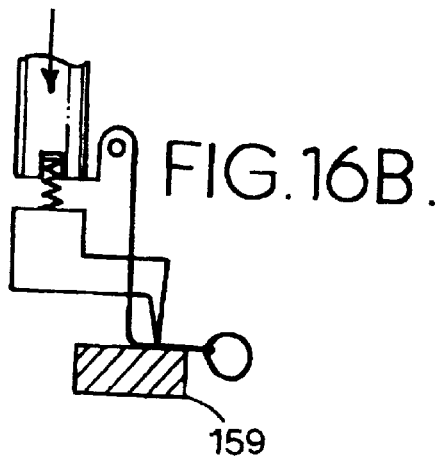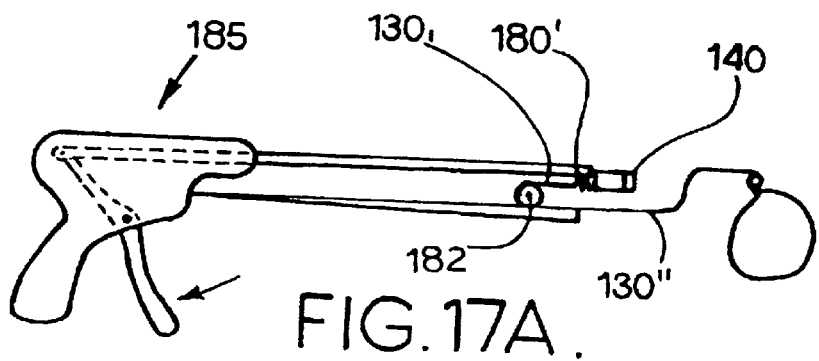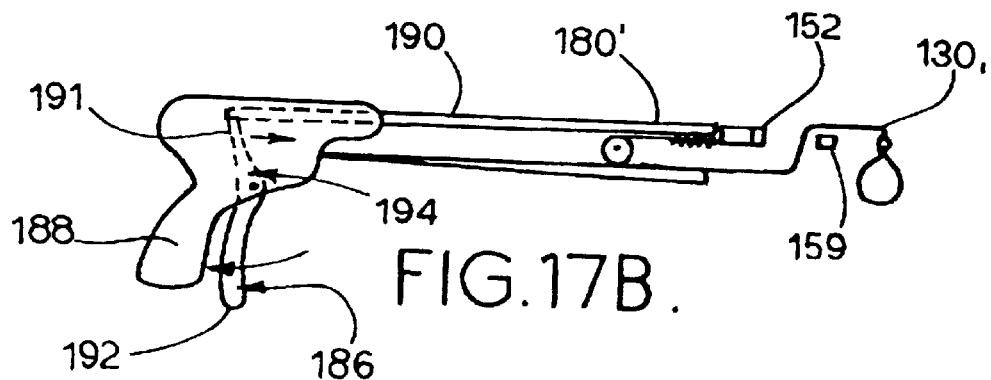

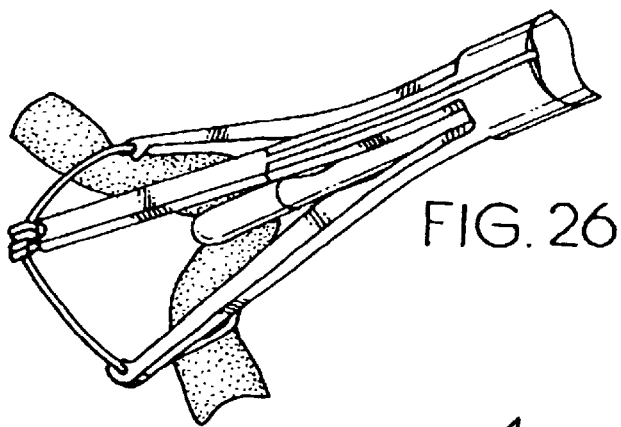
FIG. 26D.
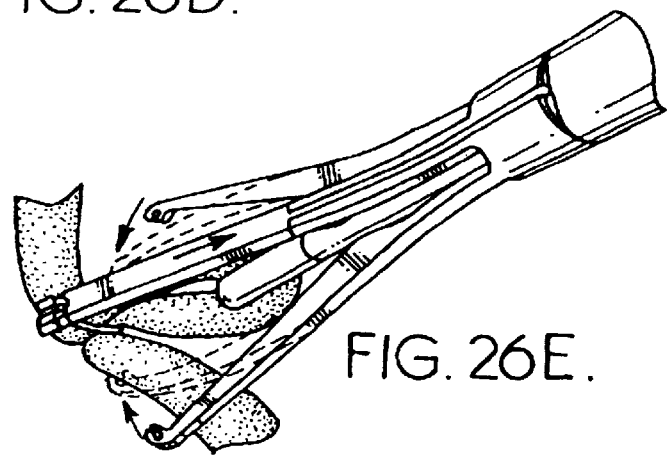
FIG. 26E.
FIG. 26H.
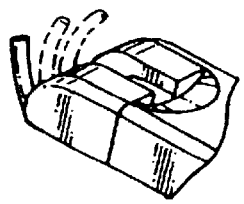
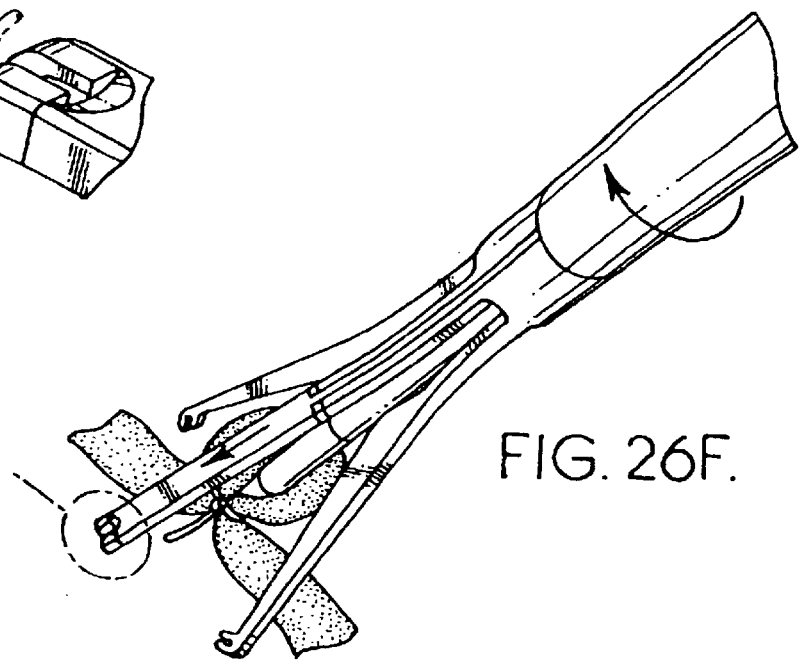
FIG. 26F.

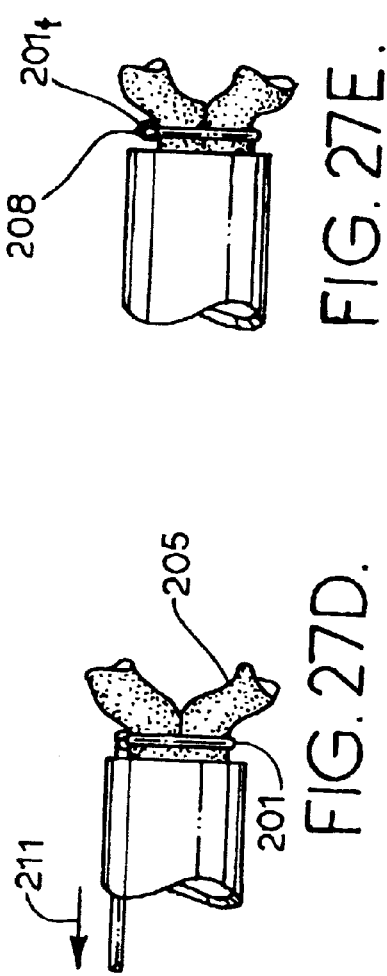
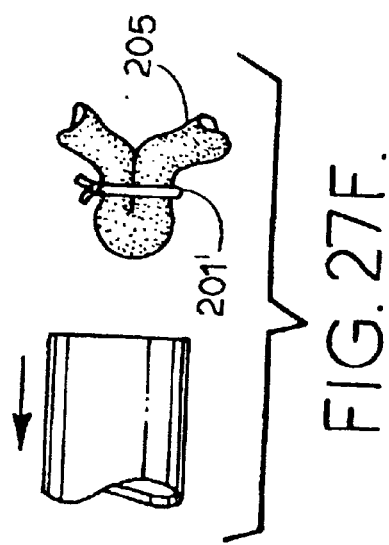
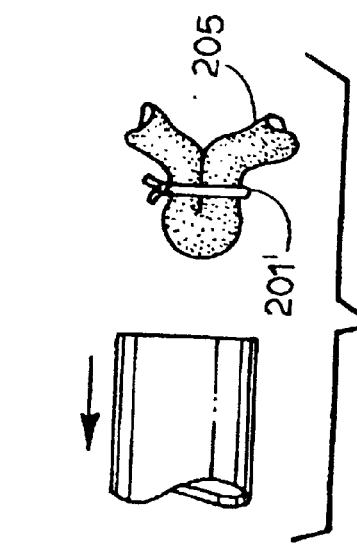
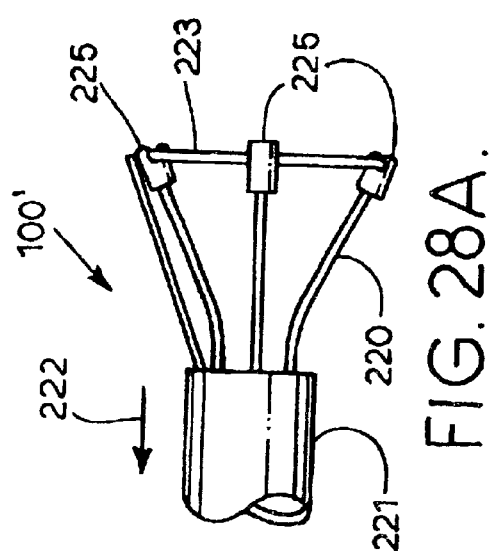
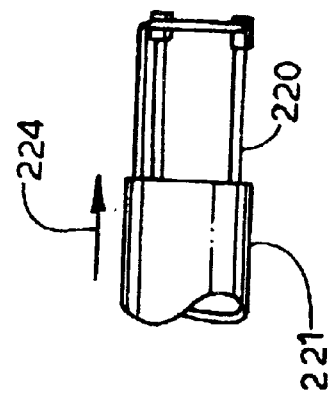

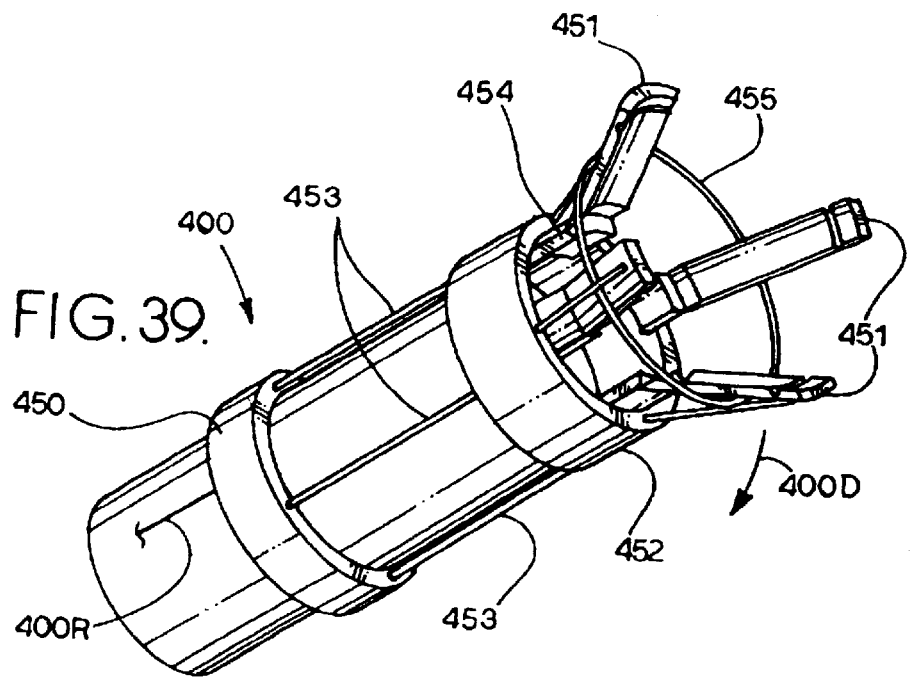
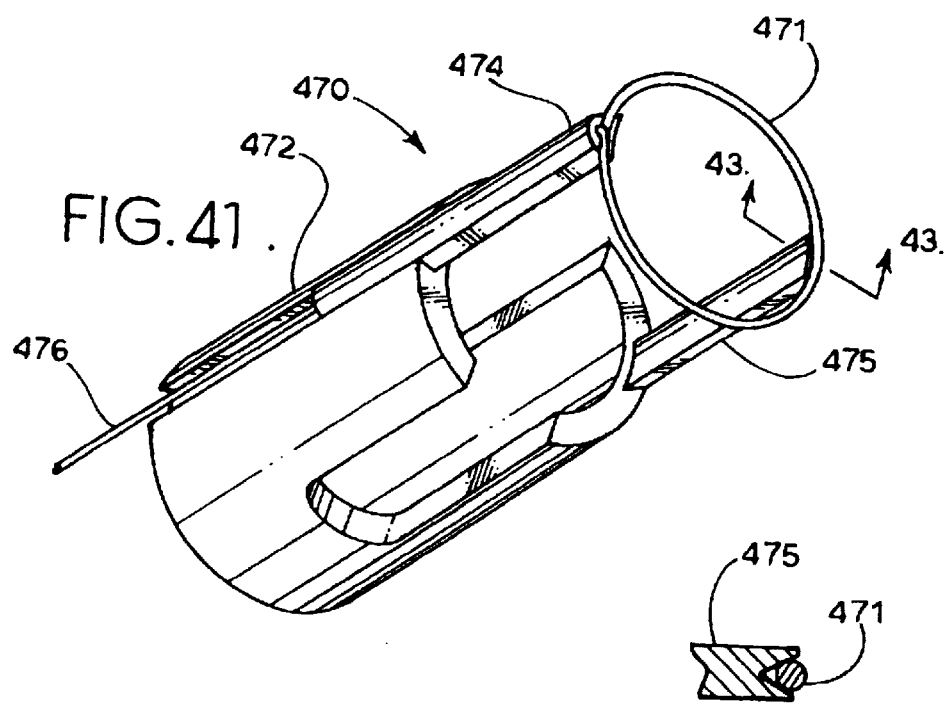

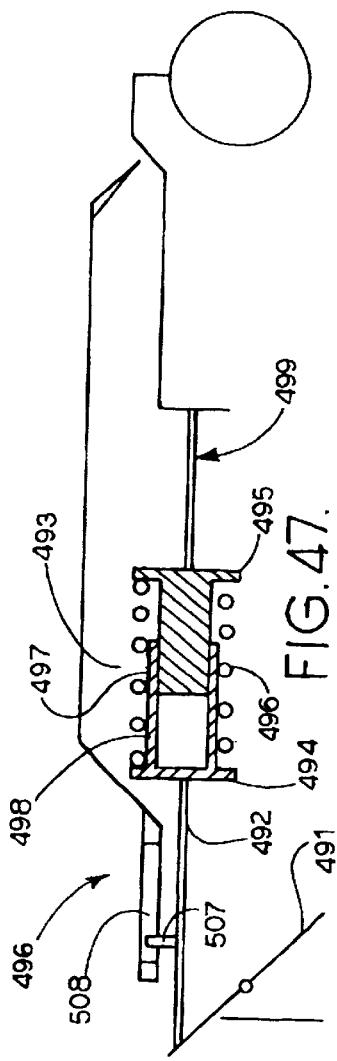
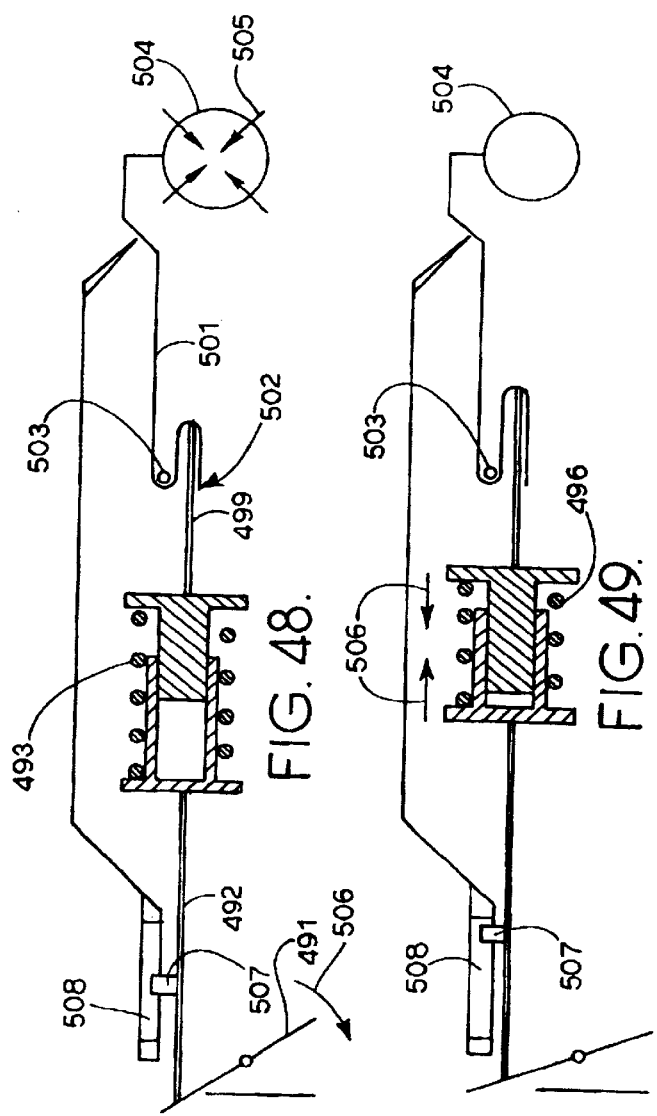

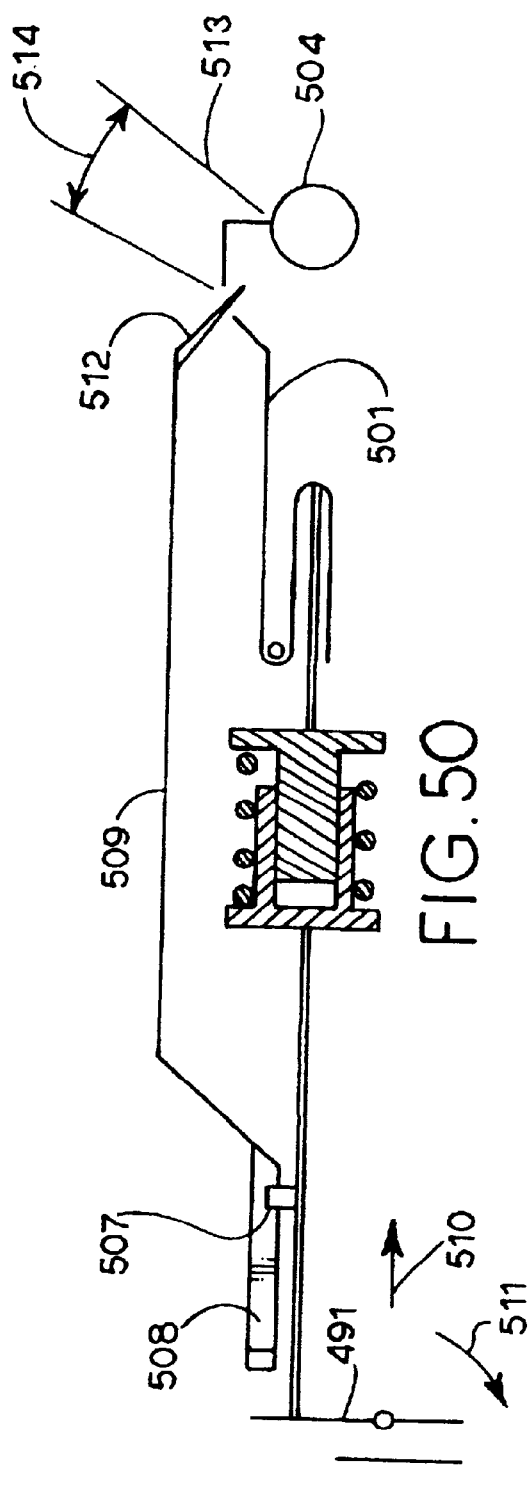
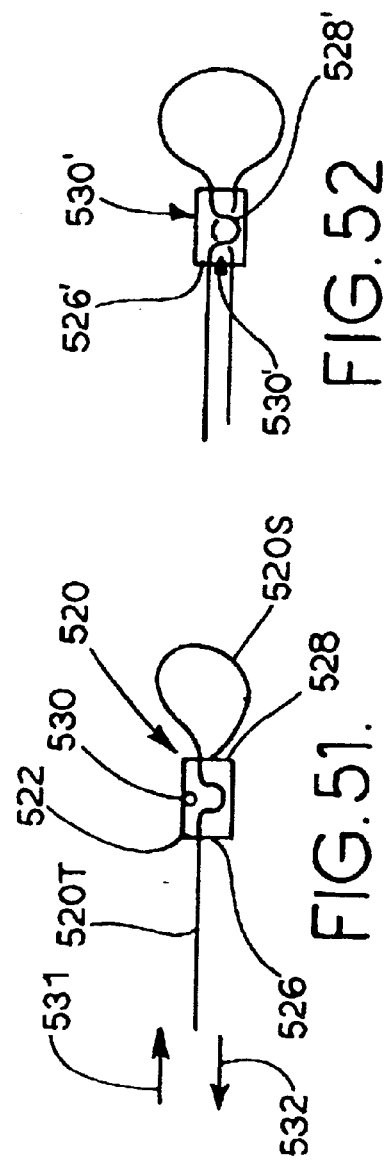

SURGICAL LOOP DELIVERY DEVICE

CROSS-REFERENCE TO RELATED APPLICATIONS

This application is a continuation application of application Ser. No. 09/241,394, filed Feb. 2, 1999 (now U.S. Pat. No. 6,152,936), which is a continuation-in-part application of U.S. application Ser. No. 09/071,811, filed May 5, 1998 (now U.S. Pat. No. 5,873,876), which is a continuation application of U.S. application Ser. No. 08/717,990, filed Sep. 23, 1996 (now U.S. Pat. No. 5,766,217). The disclosures of each of these prior related patent applications are hereby fully incorporated by reference herein.

TECHNICAL FIELD OF THE INVENTION

The present invention relates to the general art of surgery, and to the particular field of ligating tissue targets.

BACKGROUND OF THE INVENTION

As discussed in the parent disclosures which are incorporated herein by reference, many modern surgical procedures utilize small incisions through which instruments are inserted to perform the surgery in a minimally invasive manner.

One surgical technique delivers a suture loop to a tissue target, such as a polyp or the like. The loop is then placed around the target and the target is garrotted. The loop must be held open long enough and with sufficient size and stability to encircle the target and then must be managed to be efficiently tightened around the target. This is difficult to carry out in the environment associated with minimally invasive surgery. In some cases, it requires more than one person to effect the target garrotting, and even then can be onerous since the loop must remain open and in a stable configuration suitable for carrying out the procedure.

The parent disclosures discuss several prior art devices and techniques for effecting a ligating surgical technique. However, these prior techniques are difficult to carry out due to the problems mentioned above. The devices disclosed in the parent disclosures overcome these problems.

However, there is still room to improve the means and method disclosed in the parent disclosures. For example, the instruments used in the minimally invasive surgery are usually quite small; in fact, a five millimeter size is common. As the instruments get smaller, new problems are presented. Some tissue targets may actually be larger than the instrument. It may be difficult to capture large targets, especially using the prior devices such as discussed in the parent disclosures.

Therefore, there is a need for a suture ligating instrument which can be used in minimally invasive surgery, yet can accommodate tissue targets which are large in comparison to the device.

Still further, it is important for the ligature loop to be stable during insertion and setting. Ligature loop stability is achieved in the devices disclosed in the parent disclosures by locating the suture loop inside a hollow device. This works well when the target tissue is smaller than the device or can be efficiently drawn into the device.

If the device for ligating anatomical tissue can accommodate tissue targets larger than itself, its range of applications will be concomitantly increased. However, other considerations are required for targets that are larger than the device. For example, if the target is too large, it cannot be efficiently drawn into the device.

In some situations, it is desirable to have the instrument as small as possible. As the device, or instrument, gets smaller, the number of tissue targets larger than the device becomes larger, and the number of targets that may not be efficiently drawn into the device may also increase.

Therefore, there is a need for a suture ligating instrument which can be used in minimally invasive surgery and can efficiently accommodate large tissue targets, including targets that are larger than the device and targets that may not be drawn into the device in an efficient manner.

If the suture loop must accommodate a tissue target larger than the device, manipulation of the loop, including tightening the loop and cutting the suture material, must be carried out outside of the device. Since the prior devices do not accommodate such large tissue targets, they have no means for such outside loop manipulation.

Therefore, there is a need for a device for ligating anatomical tissue which can accommodate tissue targets larger than itself and which can effectively manipulate the surgical loop, even if that loop is located outside the main body of the device.

While holding the suture loop open in a stable manner is necessary, it is also necessary for an expeditious process that the loop also be handled in a stable manner so it will encircle and close about the target in a precise and accurate manner. At the present time, the inventors are not aware of any system that integrates a tissue manipulator with a suture loop holder. While the prior art does include loops on loop holders, these loop holders have several drawbacks, including allowing the loop to twist during manipulation, as well as the difficulty of maintaining the loop and the tissue properly oriented with respect to each other. Furthermore, a flaccid loop is often produced by these prior art devices.

In the environment of interest here, the thin, flexible and flaccid suture loop is extremely susceptible to collapsing prior to target acquisition. This presents a very difficult and frustrating problem to the surgeon. Furthermore, ligature loop stability becomes more difficult the larger the loop. Loop stability is not a problem in the devices disclosed in the parent disclosures since the loops are supported on the inside of the device. However, if the loop is to be used in connection with tissue larger than the device, the loop must be moved outside the device. Once the loop is moved outside the device, it cannot be supported in the manner disclosed in the parent disclosures. Loop support thus becomes a problem.

Therefore, there is a need for a system that can manage both tissue and the loop whereby the loop and the tissue remain properly oriented with respect to each other as required for an efficient ligating procedure, and which moves and controls the suture loop movement between an open configuration and a target encircling location in an accurate and precise manner. There is also a need for a device for ligating anatomical tissue which maintains a suture loop stable even for surgical targets that are large with respect to the device in which the loop must be located outside the body of the device for some portion of the procedure. Of course, this stability should be present during the entire procedure from initial insertion through and including garrotting the target.

Some targets will be smaller than others, and hence the device must be able to accommodate both large and small targets. Furthermore, since the target size may vary from extremely small to large and inflamed, the loop must be amenable to capturing a target that may have a size varying over a fairly large range. Therefore, there is a need for device for ligating anatomical tissue in which the loop and suture material is sized and adapted to accommodate both large and small tissue targets as well as targets in between the end size targets.

It is preferred that the loop be drawn down to the target size rather than enlarged to encircle the target. If the surgical loop is to be used with both small and large targets, if the loop is enlarged to encircle the large targets, its un-enlarged size may be too large for very small targets. This may degrade the results of the procedure, alternatively, it may reduce the size of the largest target that can be encircled by the loop since loops cannot be enlarged beyond a certain ratio. That is, the ratio between the smallest size of the loop and the largest size that the loop can be enlarged to will be limited by the elastic ratio of the material and the largest size loop cannot exceed a certain limit. Thus, the smallest size target will limit the range of target sizes.

Therefore, there is a need for a device in which the largest size of tissue target will not be depenent on the smallest size tissue target that can be captured by the surgical loop associated with the device.

In most surgical procedures, it is important to maintain what is known as margins. That is, a margin of extra tissue surrounding an operative site. In some cases, it means an extra margin of tissue around the excision of a lump or tumor. In the case of ligating anatomical structures, it means an extra margin of tissue left behind as a stump beyond the ligation site. This ensures that even if there is some physical stress induced at the site, the ligated ends of the tissue will not pull through the tightened suture loop and have a failure.

Therefore, the surgeon is concerned with establishing the proper tissue margins. However, in the prior art devices, when tissue is drawn into the bore of the prior art devices, it disappears from the surgeon's view. Thus, in the prior art, it is difficult to see how far one has retracted the tissue up into the bore with the tissue grasper. This in turn makes it difficult to determine the margin between the end of the tissue and the ligating loop.

Therefore, there is a need for a device that overcomes this shortcoming by providing a sight path to the tissue being ligated.

It is important to ensure that proper tension is applied by the suture loop to a tissue target. Too much tension on the loop may damage the tissue, and too little tension on the loop may vitiate the viability of the procedure. Setting proper tension may be easy when the tissue size is known. However, as discussed above, tissue size may vary over a fairly large range.

Therefore, there is a need for a device which automatically sets the proper tension of a suture loop regardless of the size of the tissue target.

Since most instruments used for minimally invasive surgery are expensive, it would be advantageous if some parts of the instruments could be re-used. Therefore, there is a need for device for ligating anatomical tissue which has some re-useable parts.

Since minimally invasive surgery has extreme space constraints, it is extremely difficult to carry out surgical steps that require more than one set of hands. Some ligature steps have, in the past, required one person to manipulate the loop while another person manipulates the tissue grasping elements. The means and method of the parent disclosures overcome this problem for tissue that is drawn into the instrument. However, there is a need to overcome this problem for larger tissue as well.

Therefore, there is a need for a device for ligating anatomical tissue which can accommodate large surgical tissue targets while still requiring only one person to carry out the procedure.

OBJECTS OF THE INVENTION

It is a main object of the present invention to provide a device for ligating anatomical tissue that can accommodate tissue targets that are larger than the main body of the instrument.

It is another object of the present invention to provide a device for ligating anatomical tissue which has some re-usable portions.

It is another object of the present invention to provide a device for ligating anatomical tissue which has a stable loop.

It is another object of the present invention to provide a device for ligating anatomical tissue which has a stable loop which can be controlled and manipulated even though the loop is larger than the main body of the instrument.

It is another object of the present invention to provide a device for ligating anatomical tissue which has a stable loop that can be cut outside the main body of the instrument.

It is another object of the present invention to provide a device for ligating anatomical tissue which can accommodate a wide range of tissue target sizes.

It is another object of the present invention to provide a device for ligating anatomical tissue which provides a sight path from the surgeon to the tissue being ligated.

It is another object of the present invention to provide a device for ligating anatomical tissue which permits proper loop and tissue management to be effected.

It is another object of the present invention to provide a device for ligating anatomical tissue which effects stable and accurate movement of the suture loop during movement of the instrument to the target.

It is another object of the present invention to provide a device for ligating anatomical tissue which can be operated by one operator.

It is another object of the present invention to provide a device for ligating anatomical tissue which can automatically set desired tension on the suture loop.

It is another object of the present invention to provide a device for ligating anatomical tissue in which the largest size tissue target that can be accommodated is not restricted by the smallest size tissue target that is to be accommodated.

SUMMARY OF THE INVENTION

These, and other, objects are achieved by a device for ligating anatomical tissue which has a suture loop controlling means that can be expanded to a size larger than the main body of the instrument. The loop controlling means also includes means for cutting the suture material and for accommodating a wide range of surgical target sizes. The suture loop size will differ for different target sizes; therefore, the device includes means for automatically accommodating varying suture tail lengths associated with different suture loop sizes and for automatically maintaining a pre-set amount of tension on the loop for a wide range of tissue target sizes.

The device for ligating anatomical tissue embodying the present invention can be used for a wide range of surgical tissue targets, and will maintain a stable loop that can be accurately manipulated and controlled outside of the main body by one operator. The loop will be held in a stable, accurately locatable position from the time it is initially inserted into the patient's body to and through the time it is positioned around the target. This increases the range of surgical procedures that can be efficiently achieved by minimally invasive techniques.

Further, parts of the device of the present invention can be detached from the main body, and thus replaced. Therefore, some parts of the device can be re-used thereby increasing the cost-effectiveness of the device.

Still further, the device of the present invention provides a sight path between the surgeon operating the device and the tissue by providing a plurality of spaced apart fingers holding the surgical loop. This allows the surgeon to look between the fingers to see the tissue and to visually adjust the tissue margin by moving the grasped tissue in or out of the ligating loop.

With the system of the present invention, the tissue and the loop can be properly managed whereby a single surgeon can orient the tissue and the loop with respect to each other for proper ligating. By stably holding the loop open and knowing where the tissue is, the surgeon using the system of the present invention can make the combination and complete a rather difficult procedure with ease. With the additional feature of being able to maintain sight of the tissue as it is engaged in the loop and enabling the surgeon to determine proper tissue margins, the system of the present invention makes this difficult procedure easy with respect to prior art devices.

BRIEF DESCRIPTION OF THE DRAWING FIGURES

Other objects, features and advantages of the invention will become apparent from a consideration of the following detailed description and the accompanying drawings.

FIG. 2 illustrates the use of the device of the parent disclosures in connection with a tissue target.

FIGS. 3 and 4 further illustrate operation of the device of the parent disclosures.

Figure 5:
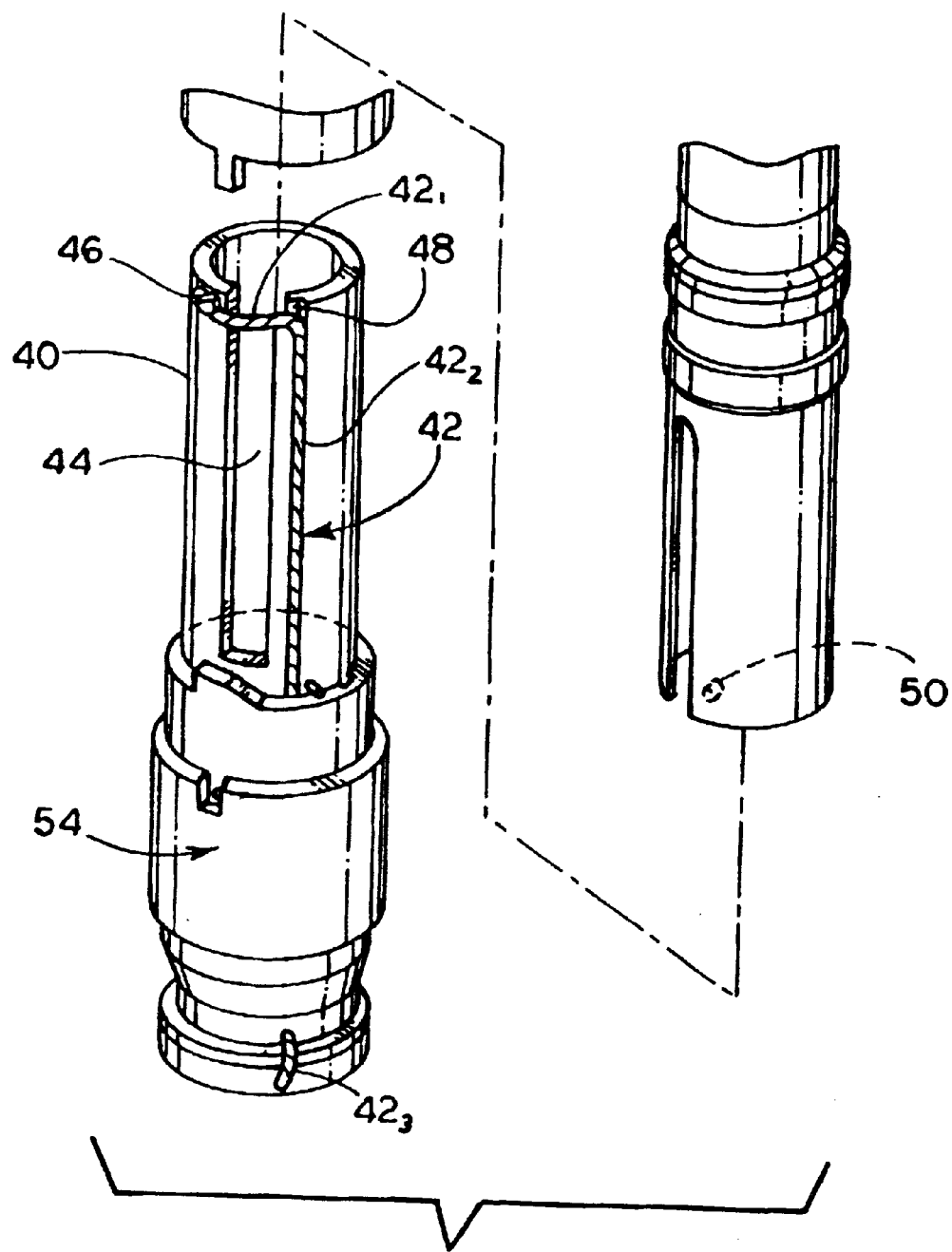

FIG. 5 is an exploded view illustrating operation of the device of the parent disclosures.

FIG. 6 is an assembled view of part of the device of the parent disclosures.

FIG. 7 illustrates operation of the device of the parent disclosures.

Figure 8A:
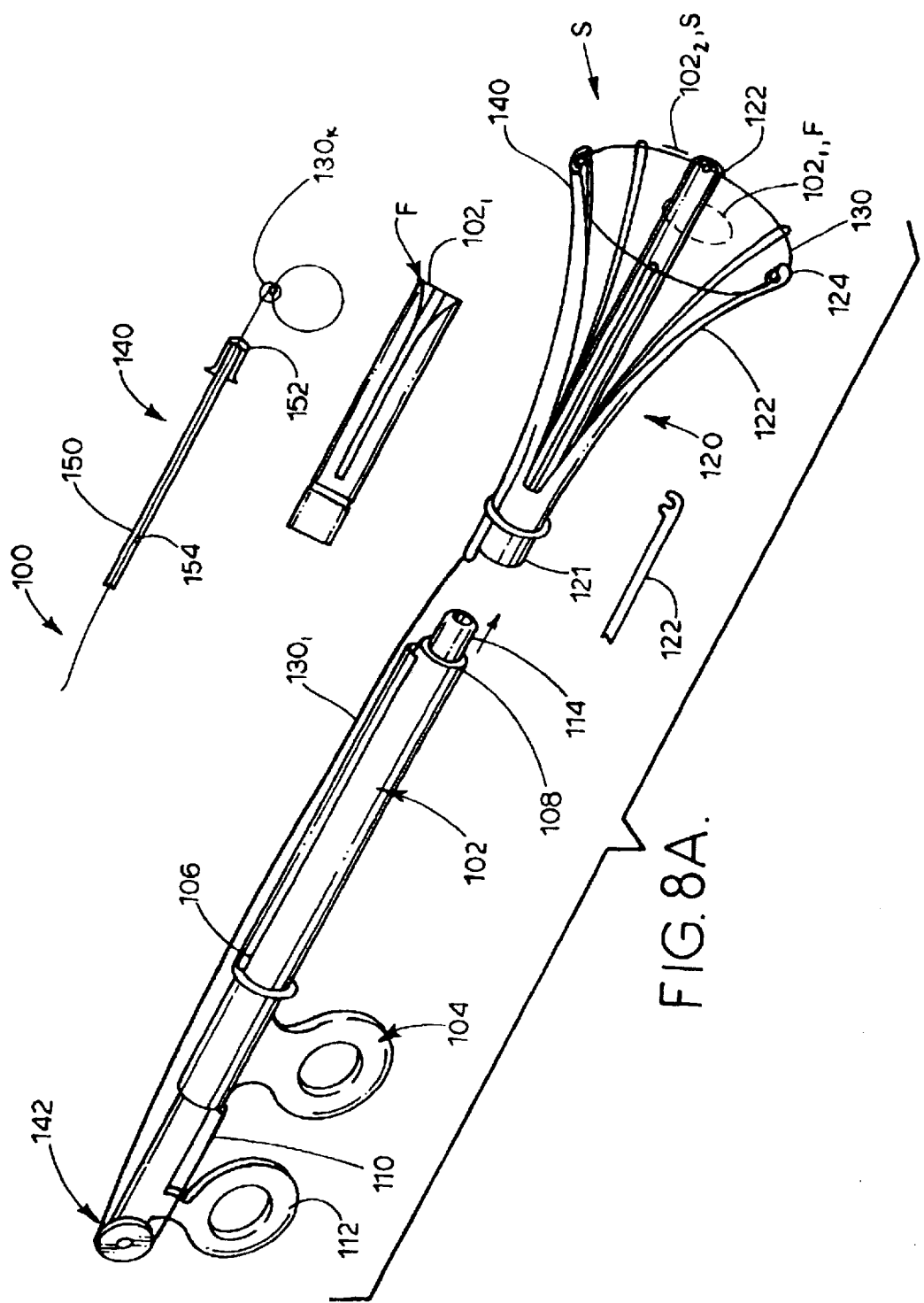

FIG. 8A is an exploded perspective view of a device for ligating anatomical tissue embodying the present invention in an open configuration.

Figure 8C:
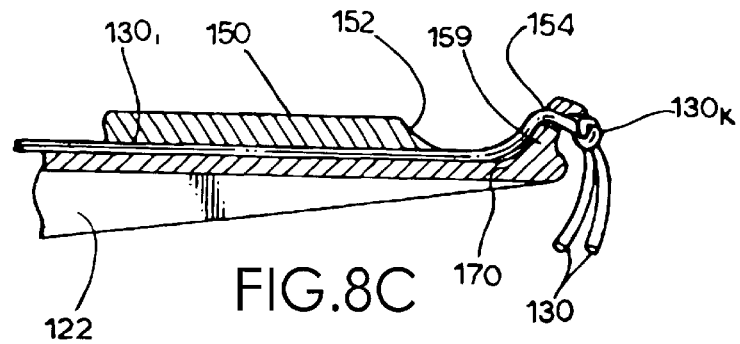
Figure 8D:
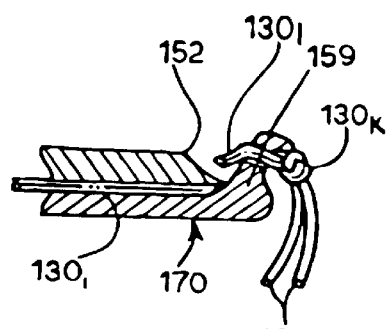
Figure 8B:
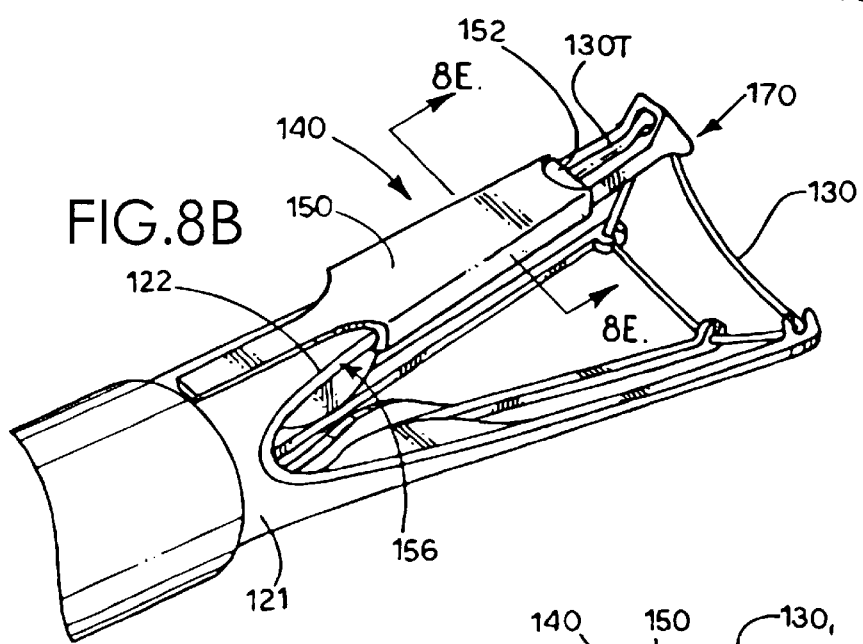

FIG. 8B is a perspective view of the distal end of the device of the present invention with a surgical loop partially open.

FIG. 8C is a side elevational view of one finger of the device of the present invention with a cutter thereon with the cutter open.

FIG. 8D is a side elevational view of one finder of the device of the present invention with the cutter in position to cut the tail off of the surgical loop.

Figure 8E:
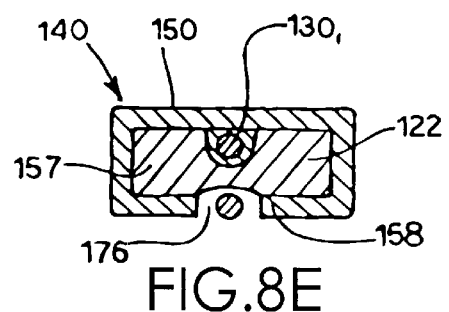

FIG. 8E is a view taken along section 8E—8E of FIG. 8B.

Figure 9:
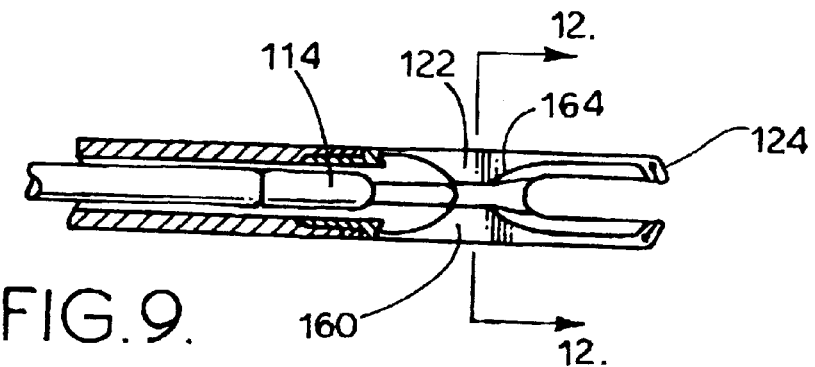

FIG. 9 illustrates the distal end of the device of the present invention in the closed configuration.

Figure 10:
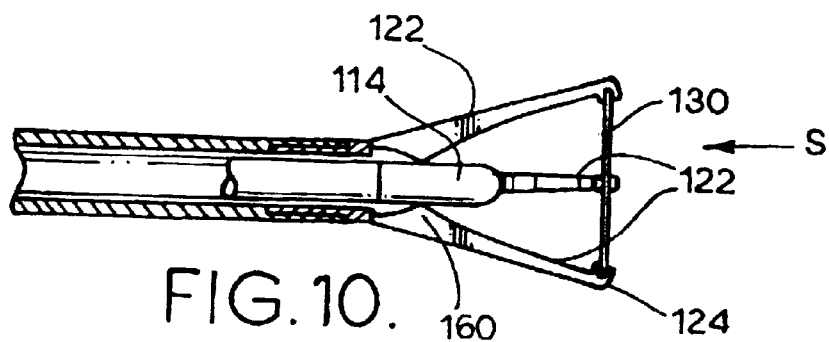

FIG. 10 illustrates the distal end of the device of the present invention in the open configuration.

Figure 11A:
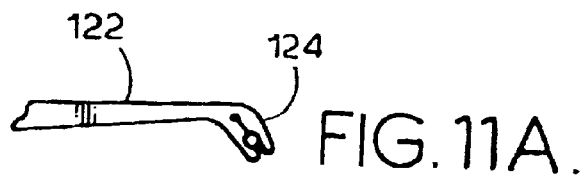
Figure 11B:
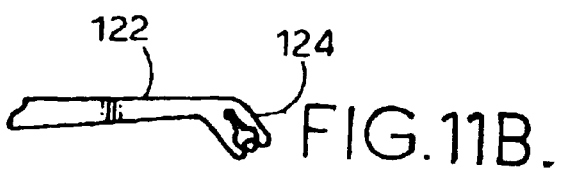
Figure 11C:
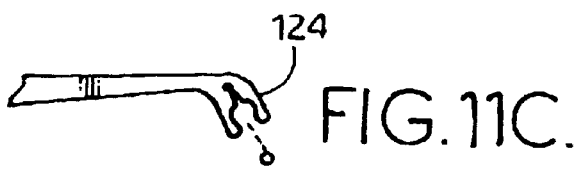

FIGS. 11A–11C illustrate a suture loop holding element of the present invention.

Figure 12:
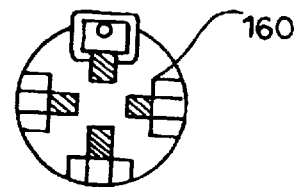

FIG. 12 is a section along line 12—12 of FIG. 9.

Figure 13:
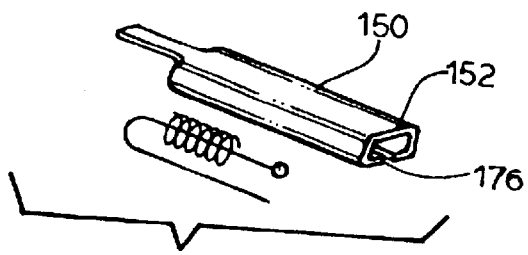

FIG. 13 is a disassembled view of a cutter used to cut suture material in the device of the present invention.

Figure 14:
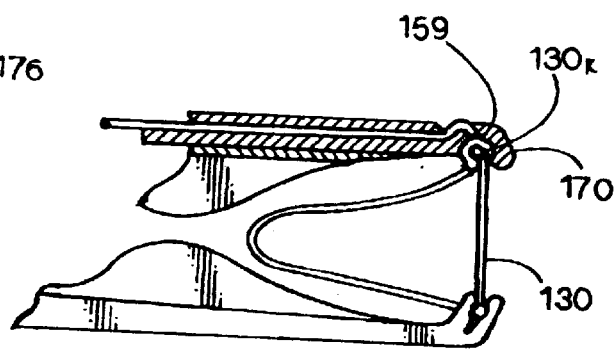

FIG. 14 is a view of a distal end of the device of the present invention illustrating the cutter element.

Figure 15:
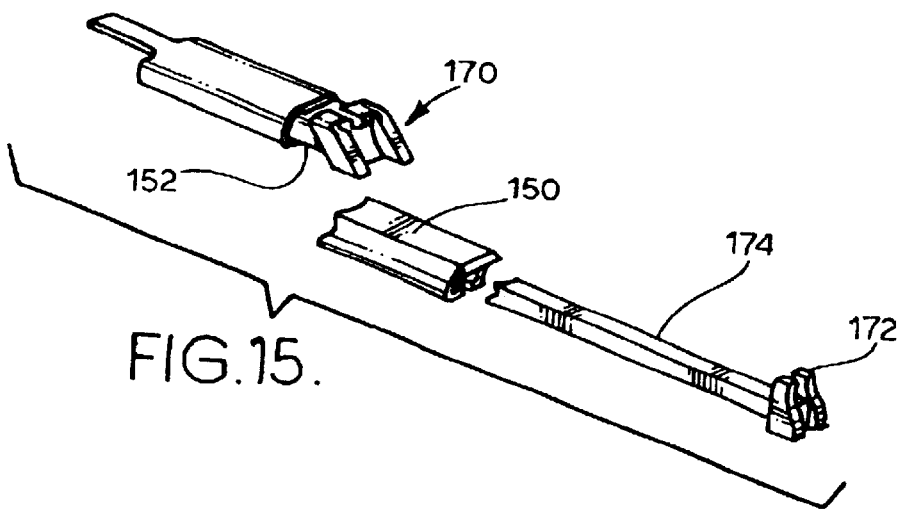

FIG. 15 is an exploded view of a cutter element of the present invention.

FIGS. 16A and 16B illustrate cutter elements of the present invention.

FIGS. 17A and 17B illustrate operation of the device of the present invention to accommodate different size tissue targets.

Figure 18:
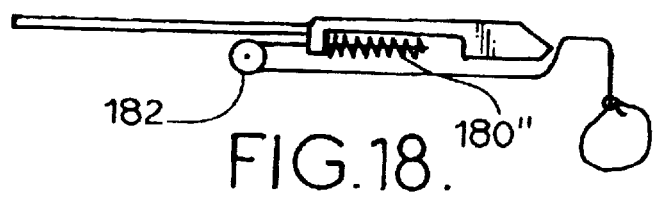

FIG. 18 illustrates an alternative form of a cutter for the device of the present invention.

Figure 19:
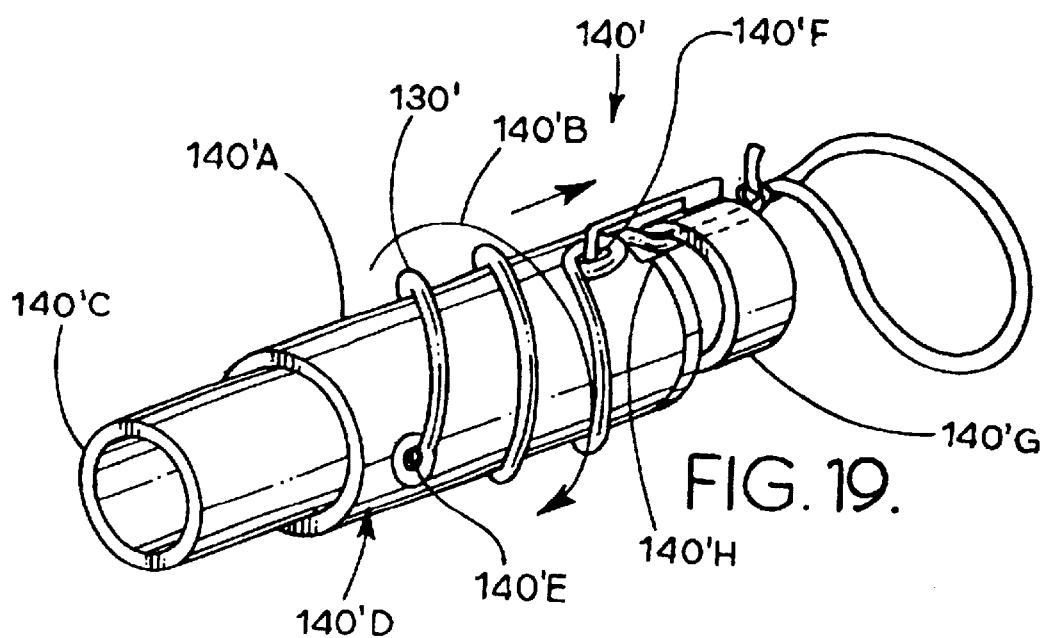

FIG. 19 illustrates an alternative form of a cutter of the present invention.

Figure 20:
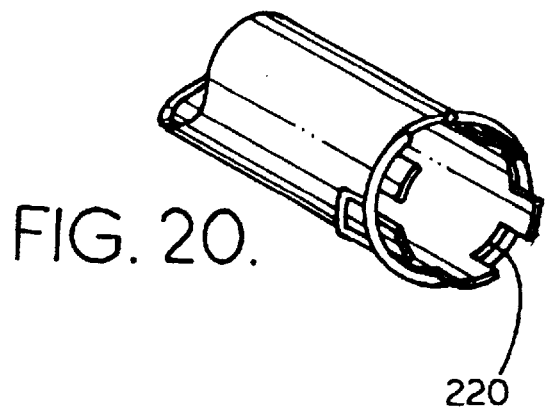

FIG. 20 illustrates an alternative form of a suture loop mounting system.

Figure 21:
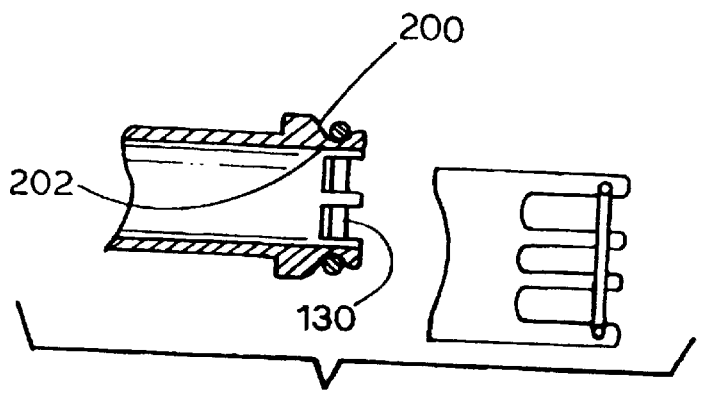

FIG. 21 illustrates an alternative form of a suture loop mounting system.

Figure 22A:
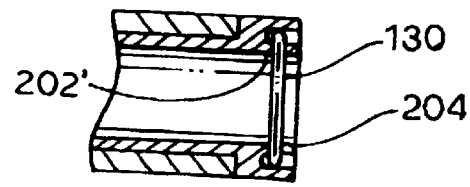
Figure 22B:
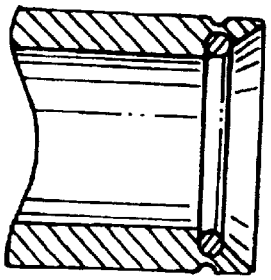
Figure 22C:
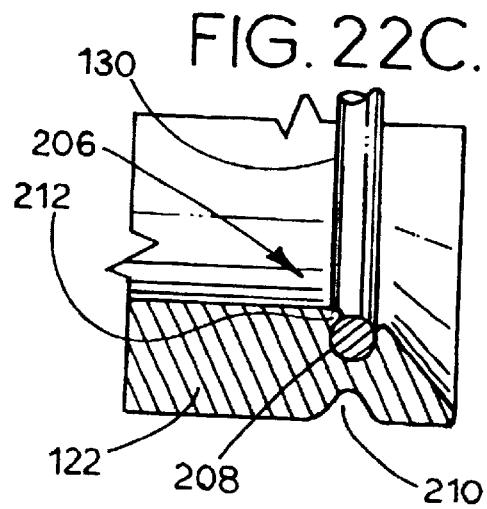

FIGS. 22A–22C illustrate a suture loop mounting system.

Figure 23A:
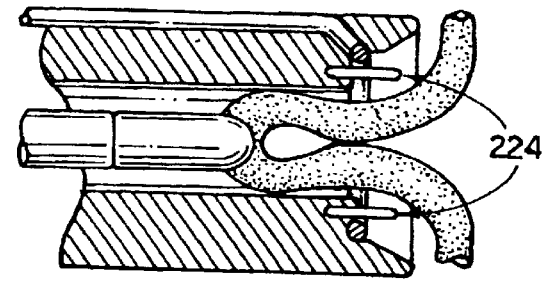
Figure 23B:
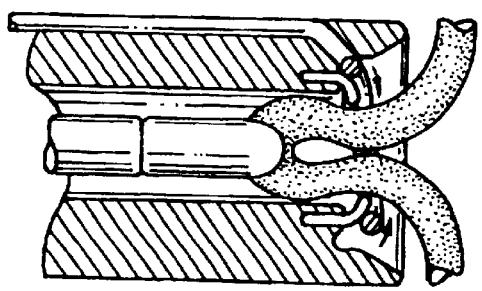
Figure 23C:
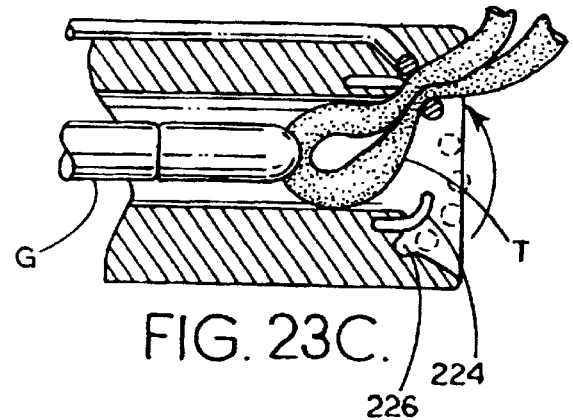

FIGS. 23A–23C illustrate operation of an alternative form of a suture loop mounting system.

Figure 24:
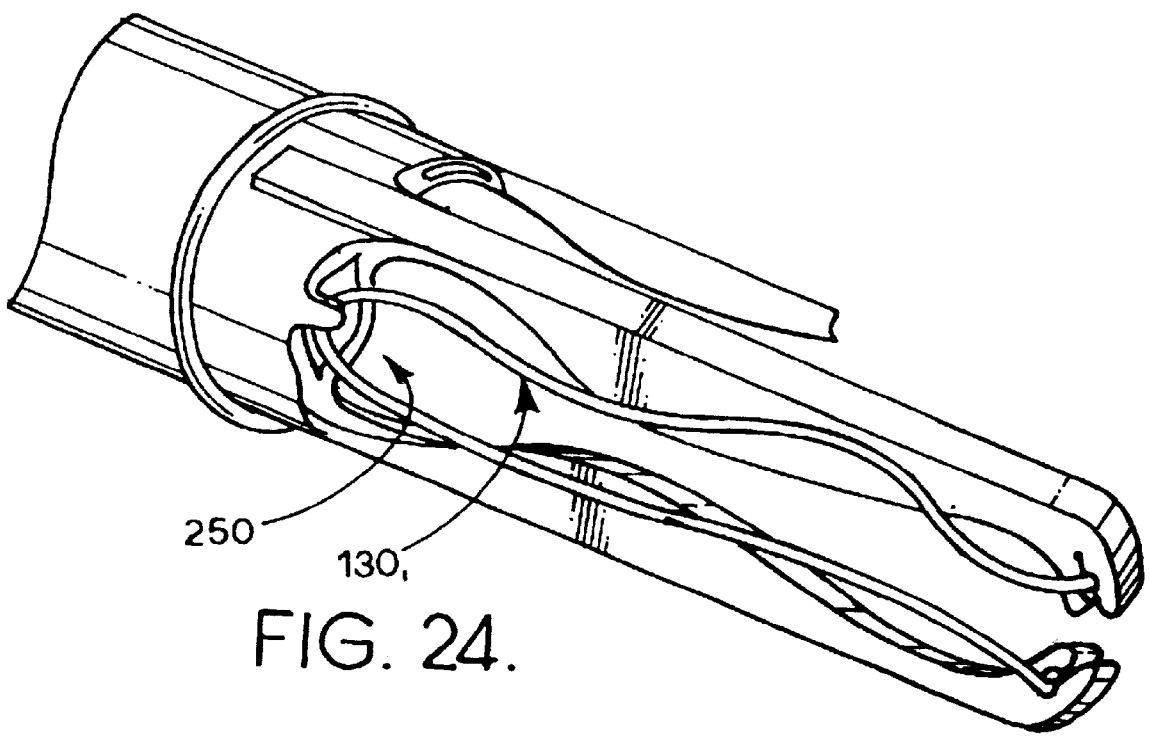

FIG. 24 illustrates a suture retaining means that can be used with the device of the present invention.

FIGS. 25A–25H illustrate operation of the device of the present invention.

FIGS. 26A–26H are perspective views illustrating operation of the distal end of the device of the present invention.

FIGS. 27A–27F show an alternative form of the device of the present invention in which the suture loop is supported on the outside of the body.

FIGS. 28A and 28B show another form of the device of the present invention in which the suture loop is supported on flexible fingers that are biased outward and are held inwardly by a tube.

Figure 29:
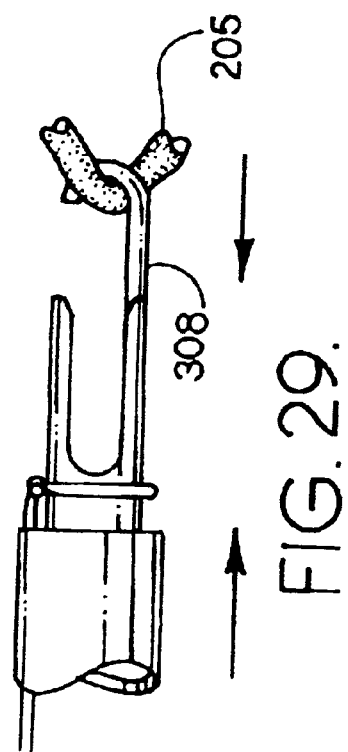

FIG. 29 shows a J-shaped tissue grasping element in combination with the device shown in FIGS. 27A–27F.

Figure 30:
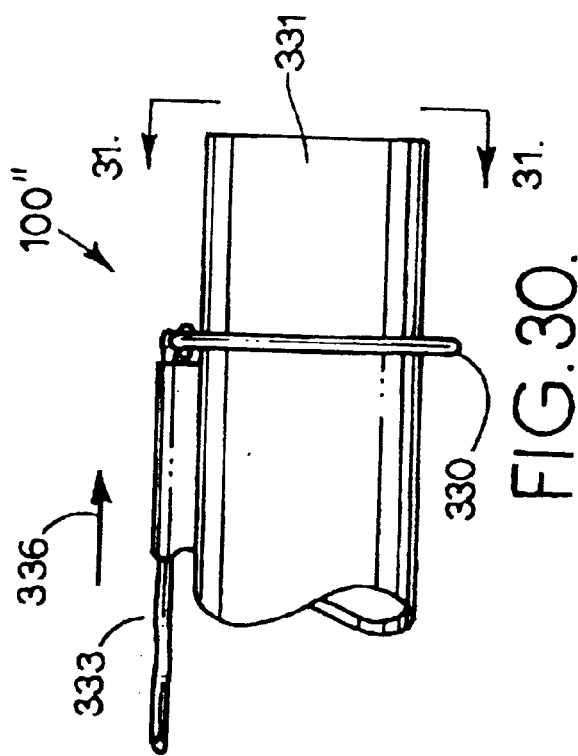
Figure 31:
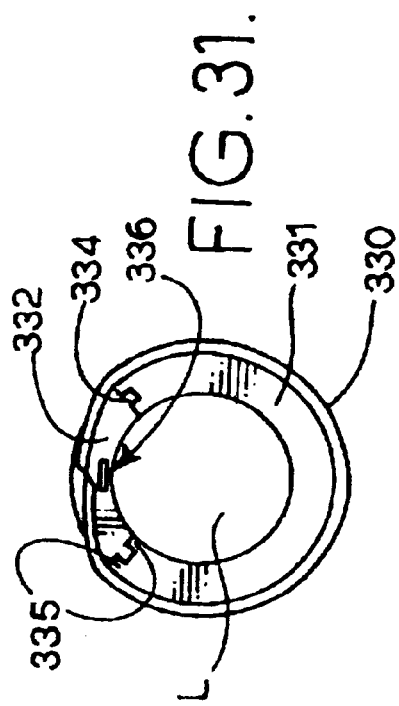

FIGS. 30 and 31 show yet another form of the device of the present invention, with FIG. 31 being a sectional view taken along line 31—31 of FIG. 30.

Figure 32:
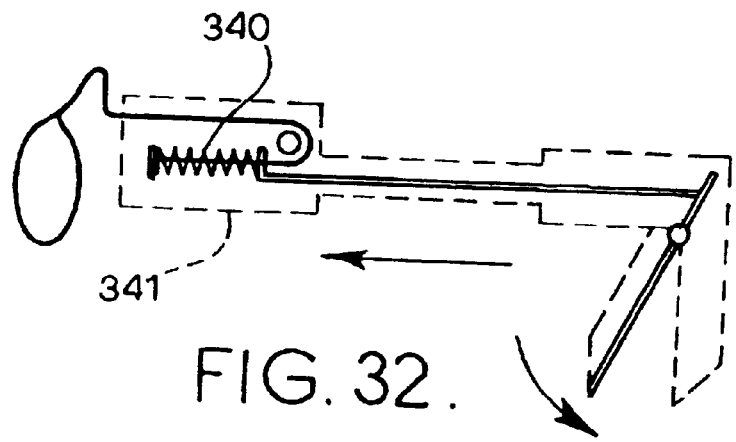
Figure 33:
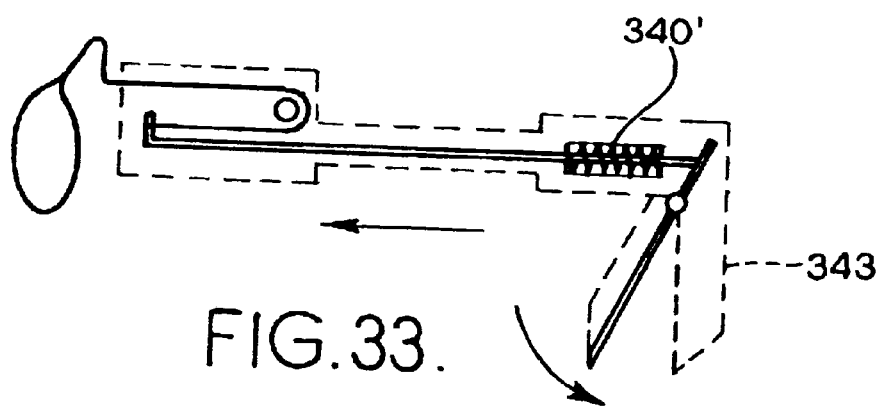
Figure 34:
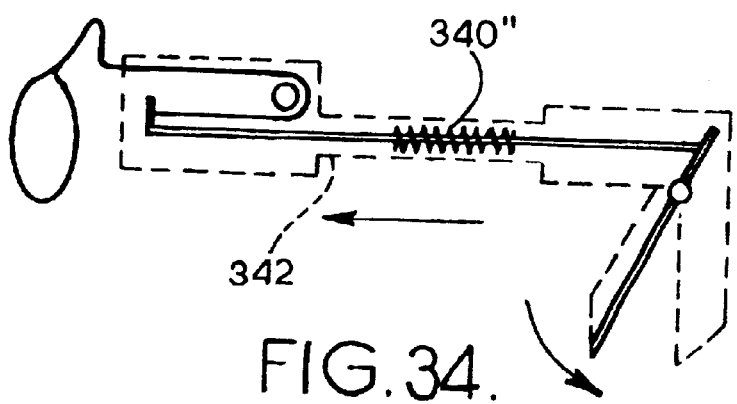

FIGS. 32–34 show various locations for a tolerance take-up mechanism used in the device of the present invention.

Figure 35:
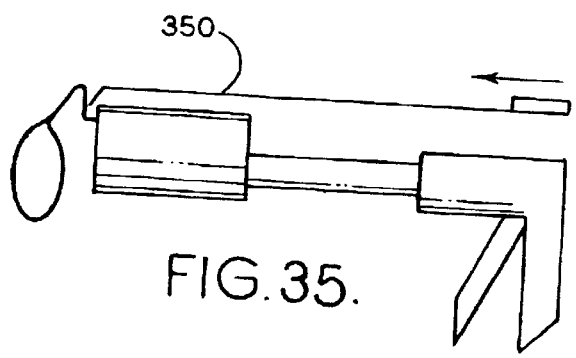
Figure 36:
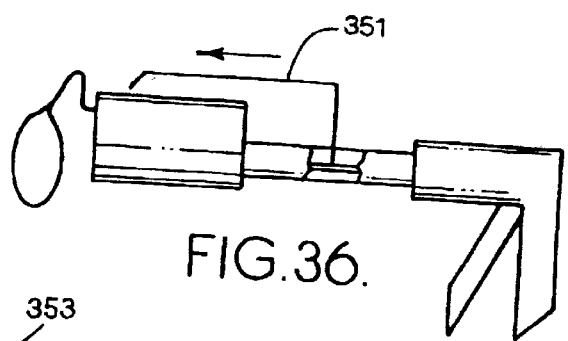
Figure 37:
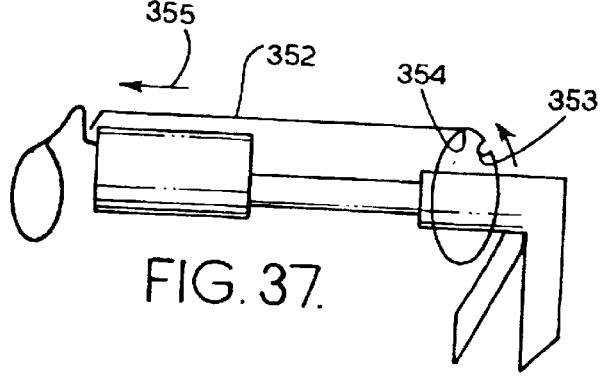

FIGS. 35–37 show various suture cutting elements for use in the device of the present invention.

Figure 38:
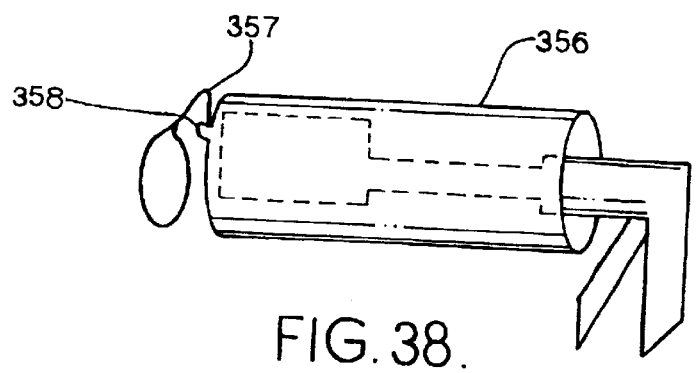

FIG. 38 shows a manual cutting sleeve for use with the device of the present invention.

FIG. 39 is a perspective view of the distal end of another form of the device in which the loop is located on the outside of the body.

Figure 40:
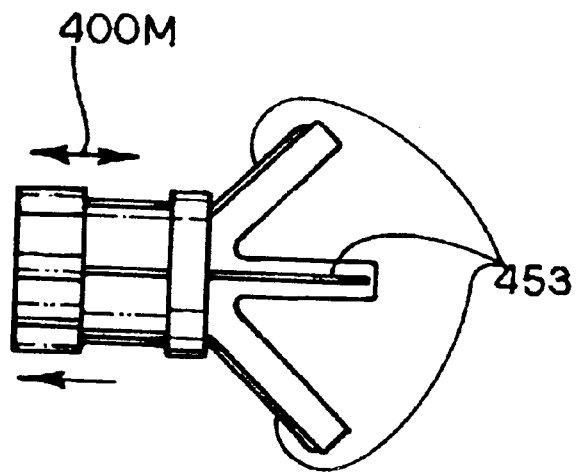

FIG. 40 is an elevational view of the distal end of the device shown in FIG. 39.

FIG. 41 is a perspective view of yet another form of the invention.

Figure 42:
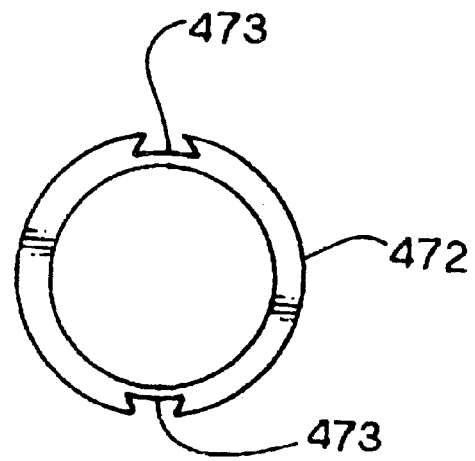

FIG. 42 is an elevational view of the body of the device shown in FIG. 41.

FIG. 43 is a view taken along line 43—43 of FIG. 41.

Figure 44:
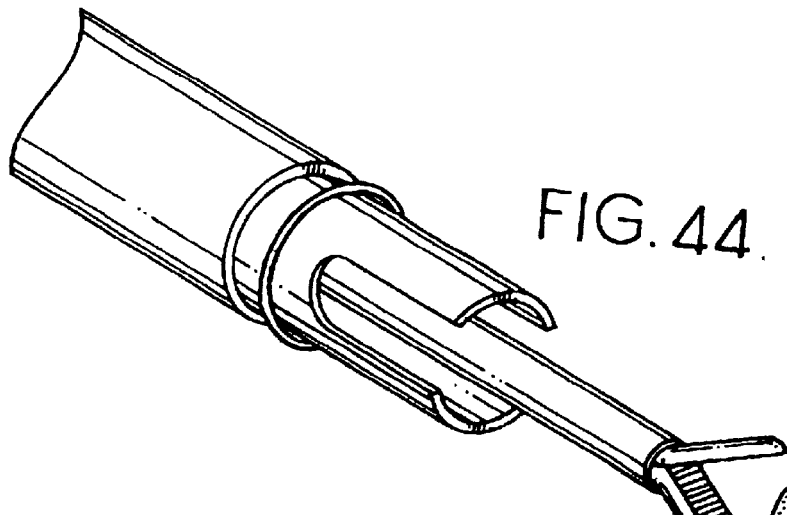
Figure 45:
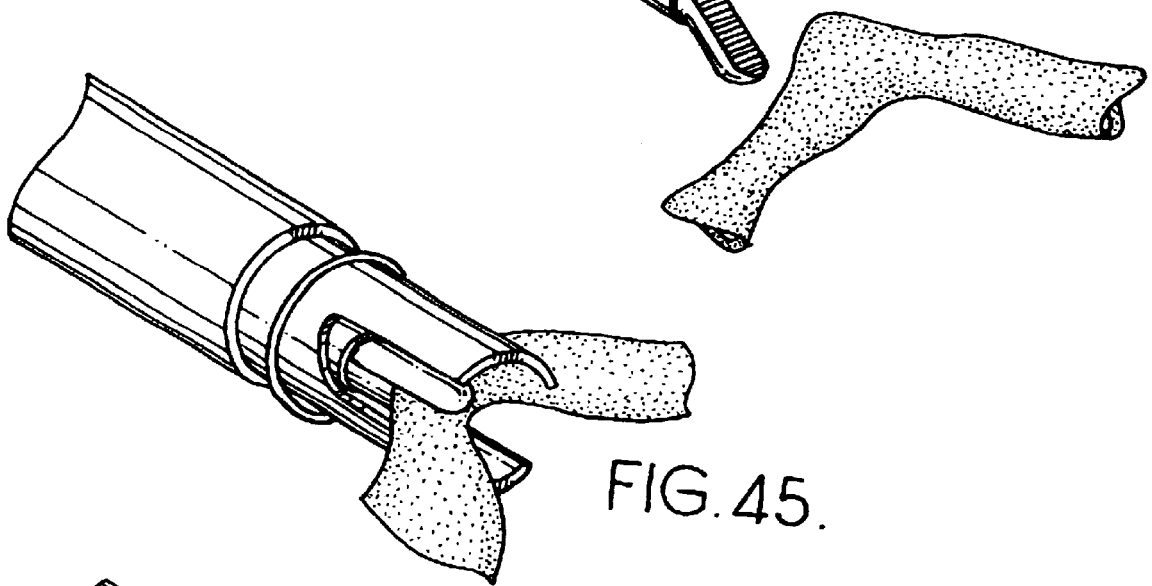
Figure 46:
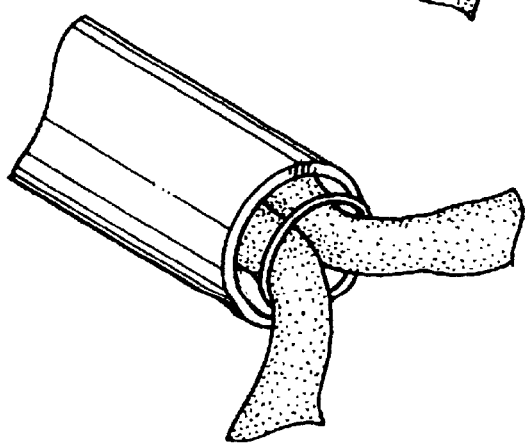

FIGS. 44–46 are perspective views of the distal end of an alternative form of the device of the present invention with a surgical loop on the outside of the body.

FIGS. 47–50 are schematic views illustrating operation of a system for automatically maintaining a pre-set tension on the suture loop over a wide range of tissue target sizes.

FIGS. 51 and 52 illustrate alternative forms of a running element for attaching the suture loop to the suture tail.

DETAILED DESCRIPTION OF THE PREFERRED EMBODIMENT OF THE INVENTION

By way of background, a summary of the operation of the preferred form of the device disclosed in the parent disclosures will be presented. A full disclosure thereof is presented in the parent disclosures and is incorporated herein by reference.

Figure 1:
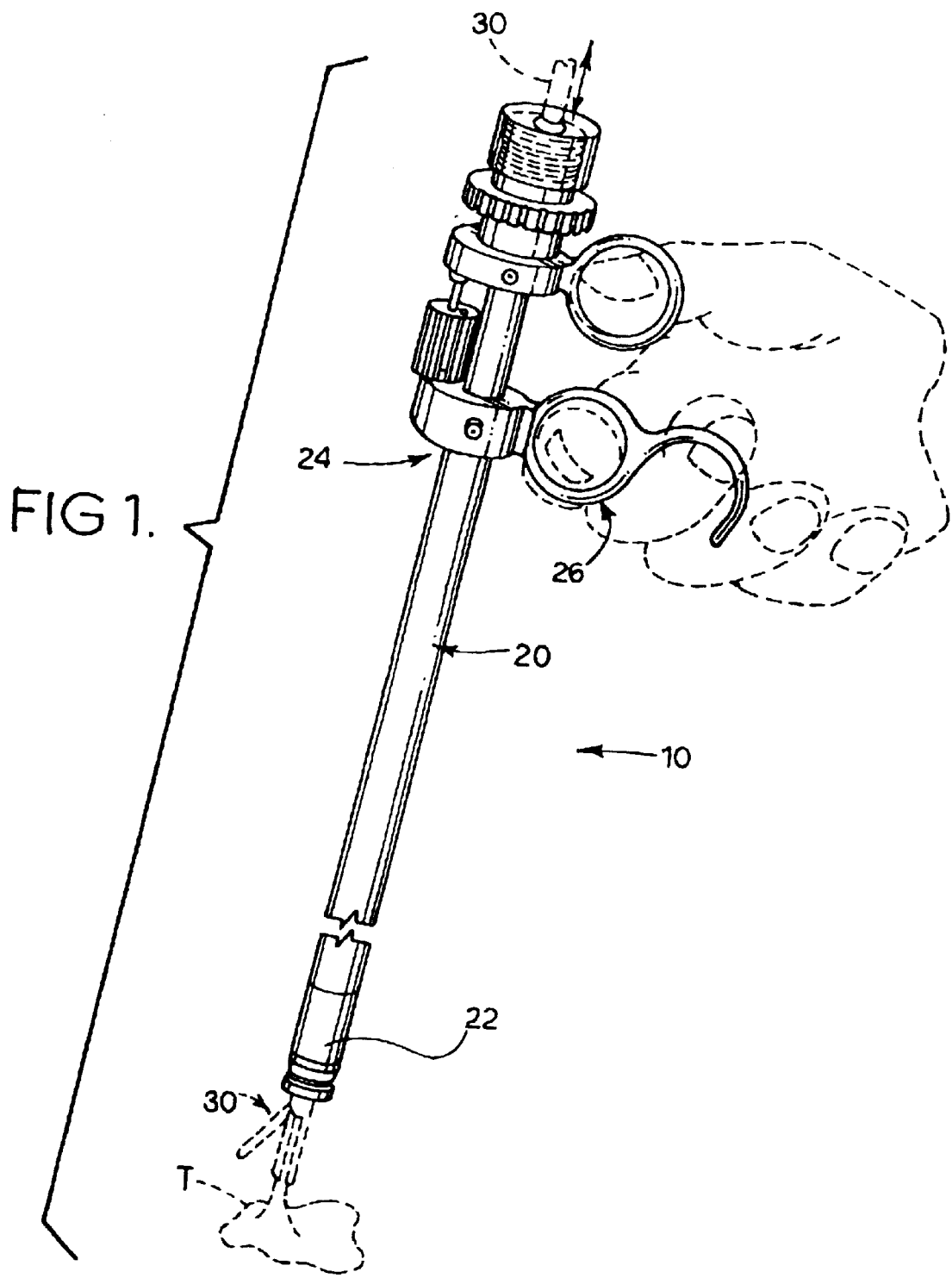
FIG. 1 shows an assembled device of the parent disclosures.

A surgical loop delivery device 10 disclosed in FIG. 1 of the parent disclosure is also shown in FIG. 1 herein and reference is made thereto, along with FIGS. 2–7 herein. Device 10 includes a main body 20 having a distal end 22 that will be located in a patient during the procedure and a proximal end 24 that will be accessed by a surgeon during a procedure. A hand-grip 26 is mounted near proximal end 24 to be available to a user's hand. A tissue grasping instrument 30 extends through device 10 to engage and grasp tissue T and draw that tissue into the instrument as indicated in FIGS. 1–3.

Referring to FIG. 5, it can be seen that device 10 includes a suture supporting element 40 on which suture 42 is mounted to extend across a slot 44 and be anchored thereto by element 46 and groove 48. Tube 20 is movable relative to element 40, and device 10 includes a projection 50 that moves into slot 44 when device 10 is operated and engages suture portion $42_1$ in the distal direction. Suture 42 is slidably held on element 40 so portion $42_2$ of suture 42 slides in the proximal direction when device 10 is operated to ligate tissue T. Device 10 further includes a suture cutter element 54 which cuts suture portion $42_2$ adjacent to a loop around tissue T after ligating that tissue. As discussed in the parent disclosures, and indicated in FIG. 5, the suture extends out of device 10 adjacent to the suture loop, then extends back into the device to intersect the cutter path. Suture portion $43_3$ is shown in FIG. 5 to indicate this suture configuration.

As indicated in FIG. 7, suture 42 includes a suture loop 56 which is mounted on an inside surface of device 10 to surround tissue T when that tissue is drawn into device 10 by tissue grasper 30. As discussed in the parent disclosures, suture loop 56 is releasably held on device 10 to have a size essentially matching the internal size of device 10, as indicated in phantom lines in FIG. 7. Suture 42 includes a running element that slidably attaches the loop to the tail, such as slip knot $42_k$, and operation of device 10 to move projection 50 distally with respect to suture portion $42_1$ draws suture portion $42_2$ proximally. Loop 56 is mounted on device 10 so slip knot $42_k$ remains stationary with respect to device 10. Therefore, proximal movement of suture portion $42_2$ draws the suture through slip knot $42_k$ thereby tightening loop 56 from the phantom line configuration in FIG. 7 to the full line configuration in FIG. 7 to garrote tissue encircled by the loop. The device is then operated to cut suture 42 adjacent to slip knot $42_k$. Device 10 is then withdrawn from the patient as indicated in FIG. 4.

As discussed hereinabove, device 10 works well, but could be improved to, among other things, accommodate tissue that is larger than the outside dimension of the device and to improve the ability of the surgeon to visualize the tissue garroting operation while still maintaining a staple suture loop. The invention disclosed herein achieves these goals.

Referring to FIG. 8A, device 100 embodying the present invention is shown. Device 100 includes a main body 102 having a first handle element 104 on a proximal end 106 thereof and a distal end 108. A suture loop operating element 110 is slidably received in main body 102 and includes a second handle element 112 which is movable toward and away from first handle element to operate device 100 and the elements thereof. Device 100 accommodates a tissue grasping element whereby a tissue manipulator and a suture loop holder and manipulator are integrated into a single unit. Device 100 is hollow and has a bore 114 extending therethrough which receives a tissue grasper for grasping tissue and orienting the device and the tissue relative to each other so a suture loop will be positioned relative to the tissue so the tissue is encircled for garroting. Various tissue graspers can be used, and the particular form of tissue grasper does not form a part of the instant invention. However, for the sake of completeness, several tissue graspers will be disclosed hereinbelow, see, e.g., FIGS. 26, 27A and 29.

Distal end 114 of suture loop operating element 110 extends out of end 108 of main body 102 and is moved in a distal direction when handles 104 and 112 are moved toward each other.

Device 100 further includes a suture loop supporting unit 120. Unit 120 includes a collar 121 which releasably engages distal ends 114 and 108 of operating element 110 and main body 102 respectively to removably mount unit 120 on device 100. A plurality of flexible fingers 122 are mounted adjacent to their proximal ends to collar 121 and extend therefrom to a distal end 124 of each finger. All fingers 122 are adapted to move distal ends 124 between a first configuration F located to be sized to be essentially equal to the outer size of the main body 102 as indicated by phantom line $102_1$ in FIG. 8A and a second configuration S located to be sized larger than the outer dimension of main body 102 as indicated by solid line $102_2$ in FIG. 8A. Various means for moving distal ends 124 can be used and several examples of these means will be discussed hereinbelow.

A suture loop 130 is releasably mounted on distal ends 124 to be moved from a first size associated with first configuration F to a second size associated with second configuration S whereby the suture loop can be moved into a size larger than the size of body 102 to capture tissue which has a size larger than the outer dimension of body 102. In this manner, any size tissue between, and including, sizes $102_1$ and $102_2$ can be accommodated by device 100 thereby providing great versatility to device 100. The suture loop is held in a stable manner so it can be accurately positioned around the target tissue.

Still further, because fingers 122 are spaced apart from each other, there are open areas between adjacent fingers, as indicated in FIG. 8A by indicator V. Open areas V provide a sight path for a surgeon located proximally of loop 130 whereby the surgeon can see the loop relative to tissue being ligated during the ligating procedure. This will permit the surgeon to locate the tissue and the loop relative to each other as necessary for proper margins, and the like.

As shown in FIGS. 8B–8E, a suture cutter 140 is mounted on one finger 122 and a suture control mechanism 142 is also mounted on device 100 for controlling the length of suture portion $130_1$. As will be understood from the teaching of this disclosure, since suture loop 130 can have a variety of sizes, the remaining suture portion $130_1$ can have a variety of lengths, i.e., suture portion $130_1$ associated with first configuration F and size $102_1$ is longer than suture portion $130_1$ associated with second configuration S and size $102_2$. Accordingly, suture control mechanism 142 automatically adjusts the length of suture portion $130_1$ based on the size of suture loop 130. Several forms of suture control mechanism 142 can be used in device 100 without departing from the scope of the present invention. Several examples of such mechanisms will be presented hereinbelow.

As discussed above with reference to the devices disclosed in the parent disclosures, cutter 140 cuts the suture adjacent to a slip knot in the suture after the suture loop has garrotted the tissue. As before, several forms of the suture cutter can be used with device 100 without departing from the scope of the present invention. As an example, cutter 140 is shown in FIGS. 8A–8E as including a body 150 slidably mounted on one finger 122 to move in a distal direction with respect to device 100 when operated. Cutter 140 further includes a cutting edge 152 on a distal end thereof and has a groove 154 defined therethrough through which suture portion $130_1$ is received. Sliding element 150 is slidably mounted on finger 122. As can be understood from FIGS. 8C and 8D, operation of the cutter device drives cutting edge 152 against an anvil 159 located on the finger associated with the cutting edge 152. Suture portion $130_1$ is located between cutting edge 152 and anvil 159 so cutting edge 152 cuts suture portion $130_1$ adjacent to slip knot $130_k$ to define a garroting loop similar to the loop shown in FIG. 4, with a tail $130_t$.

One example of a means for moving fingers 122 between first configuration F and second configuration S is shown in FIGS. 9 and 10. As shown in FIGS. 9 and 10, each finger 122 includes a cam lobe 160 near a proximal end thereof, with a living hinge 162 located near the cam lobe. As can be seen in FIGS. 9 and 10, the cam lobes define a small passageway 164 therebetween when unit 120 is in first configuration F. Passageway 164 is smaller than the outside dimension of distal end of the grasping element 114. Thus, movement of distal end 114 toward the distal end of device 100 is blocked by cam lobes 160.

However, due to living hinge 162, and because fingers 122 are fixed to collar 121 at the proximal ends thereof, abutting contact between distal end 114 and cam lobes 160 as end 114 moves distalward causes the fingers to pivot at living hinge 162 radially outward in direction $122_O$ from the FIG. 9 first configuration F toward the FIG. 10 second configuration. Fingers 122 are formed of flexible material so they will be biased by the material memory toward the FIG. 9 configuration, with the engagement between cam lobes 160 and distal end 114 preventing the fingers from returning to the FIG. 9 configuration.

An alternative form of the device can include a band of elastic material encircling legs 122 to bias those legs toward the FIG. 9 configuration. The grasper forcing the legs apart by means of engagement with the cam lobes will overcome this bias when the grasper is in the tissue grasping position, but the legs will be returned to the relaxed FIG. 9 configuration as soon as the tissue grasper is withdrawn from engagement with lobes 160.

As shown in FIGS. 9 and 10, suture loop 130 will be enlarged as fingers 122 move from the FIG. 9 configuration towards the FIG. 10 configuration. With the suture loop in the FIG. 10 configuration, a tissue grasper can grasp tissue and the grasped tissue and the loop can be oriented with respect to each other so the suture loop encircles the tissue. Once the tissue is encircled, a mechanism, such as the suture loop tightening mechanism described above with regard to device 10 disclosed in the parent disclosures, can be used to tighten the suture loop. Another loop tightening mechanism will be described below in relation to FIGS. 47–50. Slip knot $130_k$ is held stationary with respect to device 100 while suture portion $130_1$ is pulled toward the proximal end of device 100. This causes the suture to slip through knot $130_k$ to tighten the suture loop. At that time, the suture is pulled off ends 124 of fingers 122 to garrote the tissue. As shown in FIG. 15, a suture knot holder 170 can extend through cutter body 150 adjacent to finger 122 and includes a distal shoe 172 on a distal end of body 174. A proximal end of body 174 is located near handles 104 and 112 so body 174 can be moved distalward of device 100 into engagement with knot $130_k$ to hold that knot in place while cutter edge 152 is driven against the suture to cut that suture. As can be seen in FIG. 13, cutter body 150 is C-shaped and has a gap 176 defined therein. Gap 176 can be used to accommodate a finger 122 or a suture portion. The elements used to move the cutter are shown in FIGS. 25 and 35–37.

Various forms of suture control mechanisms 142 are shown in FIGS. 16A–18 and FIGS. 47–50, and attention is now directed to FIGS. 16A–18. Broadly, mechanism 142 includes a suture length adjusting element which accounts for the varying length of suture portion $130_1$ as discussed above so that longer portions $130_1'$ shown in FIG. 17B are accommodated for smaller tissue sizes T' are shorter portions $130_1''$ for larger tissue sizes T'' shown in FIG. 17A.

One form of suture length adjusting element includes a spring 180 connected at one end thereof to the distalmost end of suture portion $130_1$ and at another end thereof to cutter 140. Spring 180 expands or contracts to take up the lengths of portion $130_1$ associated with different tissue sizes. Suture portion $130_1$ is trained around a pulley 182 mounted on body 102. The cutter in FIGS. 17A and 17B will travel the same distance every stroke cutting the tail of the suture against anvil 159. The extension spring 180' acts as a clutch, elongating more when a large piece of tissue is in the loop and undergoing less elongation when a smaller piece of tissue is in the loop. Cutter 140 can be coupled to the spring in various ways, such as to an expansion spring 180' in FIGS. 16A and 17A or a compression spring 180'' in FIG. 18. Anvil 159 is shown in FIGS. 14, 16A and 16B and is mounted on the finger 122 adjacent to the cutter edge 152. Other forms of tolerance take-up means are possible, and several examples thereof are shown in FIGS. 32–34 as well as in FIGS. 47–50 and will be discussed later in connection with those figures.

As discussed in the parent disclosures, the suture extends out of the suture loop support and is wound back across anvil 159 in front of cutter edge 152. As indicated in FIGS. 17A and 17B, handles 104 and 112 can be replaced by an operating mechanism 185. Operating mechanism 185 includes a trigger 186 and a grip 188, with trigger 186 being pivotally connected to grip 188 to move with respect to the grip when operating mechanism 185 is actuated. A lever arm 190 is connected at one end thereof to trigger 186 on end 191 of the trigger. Actuating end 192 of the trigger is on one side of a pivot 194 and end 191 is on the other end of the trigger whereby moving trigger end 192 toward grip 188 moves lever 190 in a distal direction of device 100 to force cutter edge 152 against anvil 159 with suture portion $130_1$ interposed therebetween. Spring-like element 180 maintains the suture portion taut and also takes up excess suture when a smaller loop is used to ligate tissue.

In some instances, the cutter could be located proximally of the position shown for cutter 140 in FIG. 8. This location can be on the finger near the proximal end of the finger and adjacent to collar 121, or even on the collar 121 if desired. This positioning of the cutter will create a longer suture tail than the distal location of the cutter shown in FIG. 8. However, such proximal location of the cutter will permit the cutter to generate higher cutting forces than the distal location shown in FIG. 8 because the cutter will be on a more stable support.

Another form of cutting and tightening device is shown in FIG. 19 as element 140' as including a body 140'A is mounted to rotated in direction 140'B about an inner tube 140'C that is on the device, either on the main body or on the suture holding mechanism. The rotation of body 140'A takes up excess slack similar to a winch winding the suture on the outside surface of a spool 140'D. Suture tail 130' is fixed to body 140'A at an anchor 140'E and is trained around a pulley 140'F to change take-up movement of the suture between rotational and linear. After the suture is tensioned, the body is indexed distally, or the spool is moved, thereby trapping and cutting the suture between flange 140'G and cutter blade 140'H on the spool.

Other means for supporting the suture loop on device 100 includes mounting the suture loop on the outside of the device. For example, as shown in FIG. 21, suture loop 130 is supported on the outside of fingers 122' in grooves 200. A neck 202 is formed at the base of each groove. neck 202 is thin and forms a break joint which is broken when the loop is tightened about the tissue. The break-joint concept is also shown in FIG. 22A where break joint 202' is oriented to locate suture loop 130 on the distalmost end of the fingers and breaks to remove barrier portion 204 when the loop is tightened. A modified form of this break joint is shown in FIGS. 22B and 22C where joint 206 includes a groove 208 and a flexible neck 210. When the suture loop is tightened about the tissue, it pulls against wall 212 which causes the finger 122 to flex. As loop 130 is tightened, the finger flexes until the loop is pulled over wall 212 and out of groove 208.

Yet another outside-positioned suture loop supporting means is shown in FIG. 20 where outwardly curved castellations 220 support the suture loop and flex in the manner just described for wall 212 as the suture loop is tightened to release the loop. Yet another means for retaining the suture loop on the finger ends is shown in FIGS. 23A–23C and includes flexible filaments 224 inwardly adjacent to grooves 226. Filaments 224 replace walls 212 and operate in a similar manner to retain the suture loop in grooves 226 until the loop is tightened about the target tissue which has been oriented within the loop by a tissue grasper G. Movement of the suture loop is indicated by the phantom lines in FIG. 23C.

When the suture is expanded beyond a first size to open and accept larger tissue, suture portion $130_1$ is retained within device 100 by a retainer element 250 attached to the device adjacent to collar 121 and interposed between two adjacent fingers and shown in FIG. 24. Element 250 is in the shape of a hook and suture portion $130_1$ is wound around element 250 to keep it out of the way while providing sufficient suture length to permit the fingers to completely spread out when opened. Thus, when opening the suture loop the tail does not need to be drawn back through the knot.

Figure 25A:
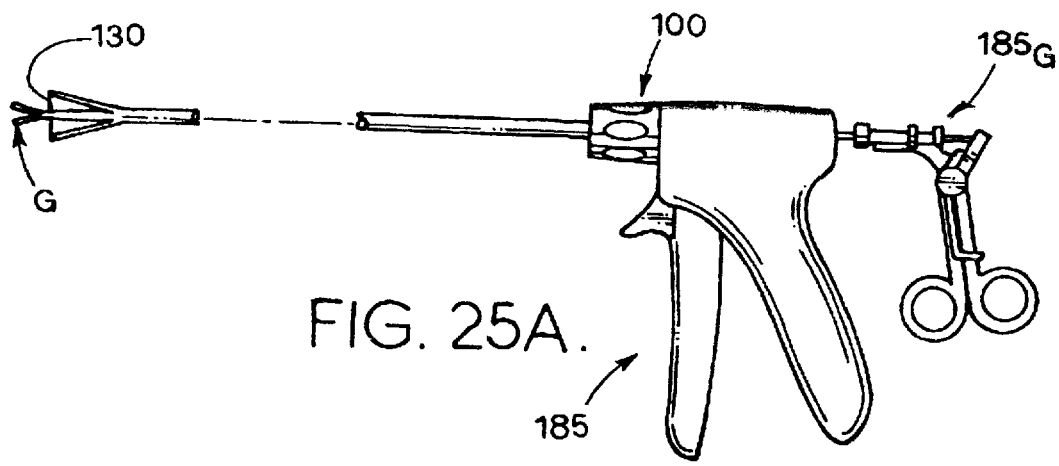
Figure 25B:
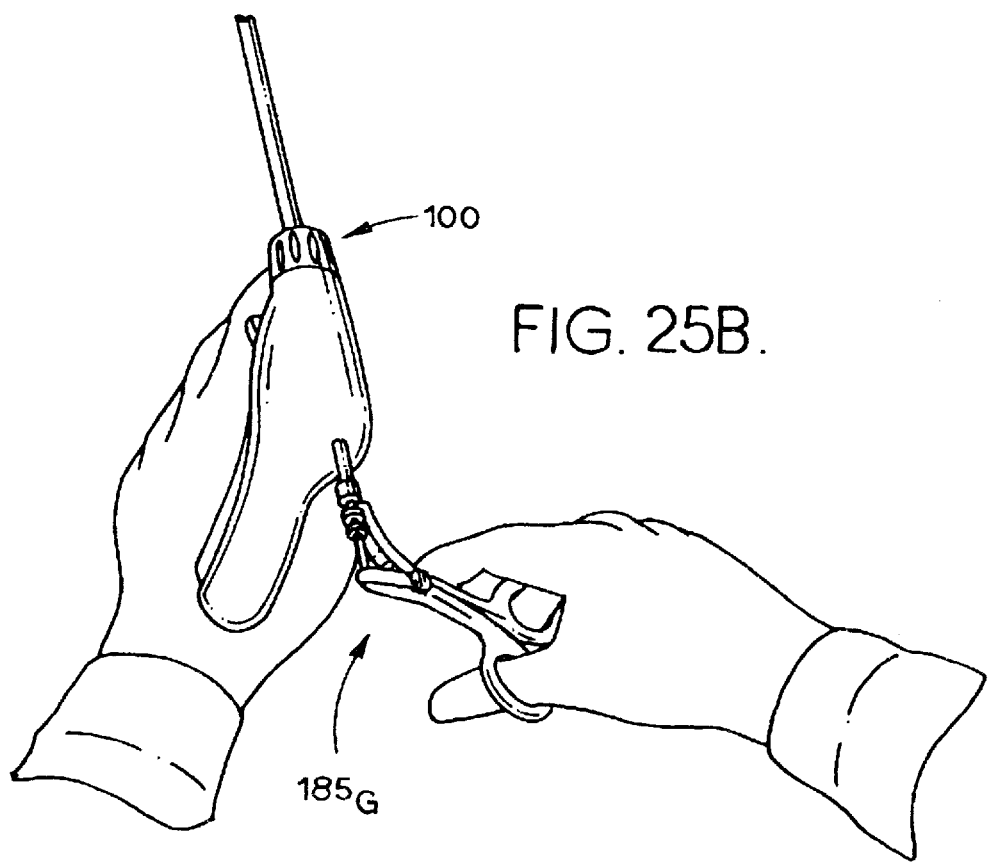
Figure 25C:
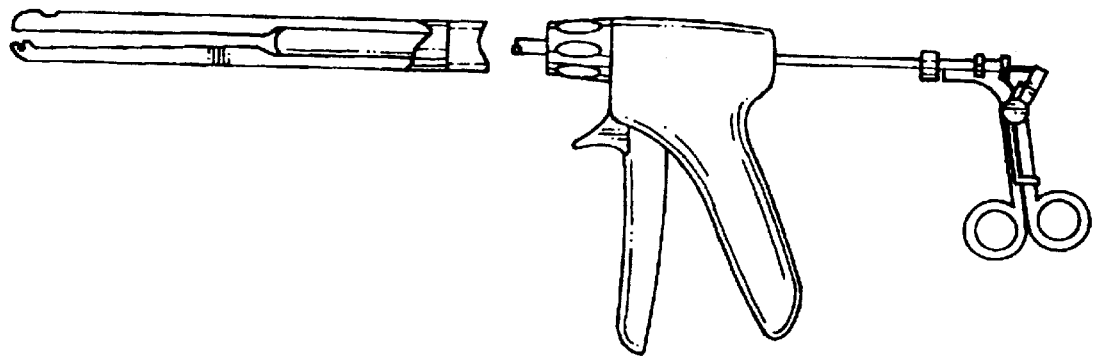
Figure 25D:
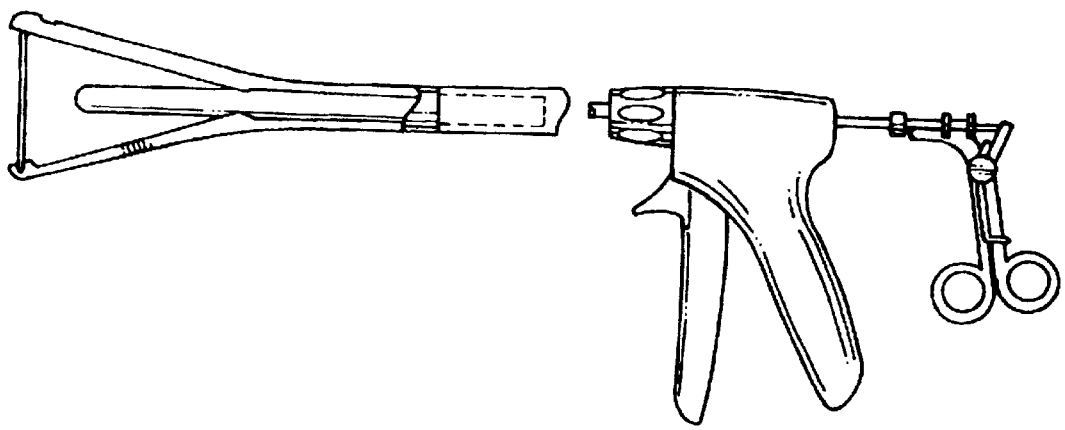
Figure 25E:
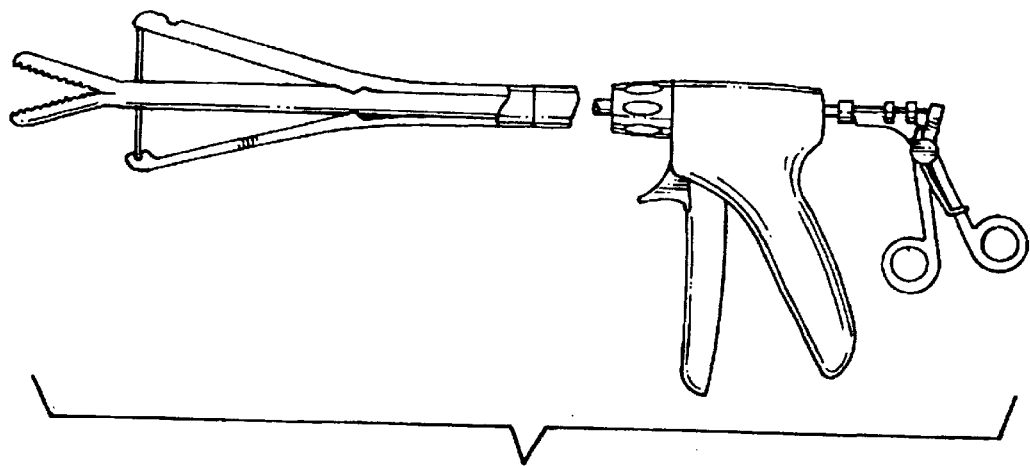
Figure 25F:
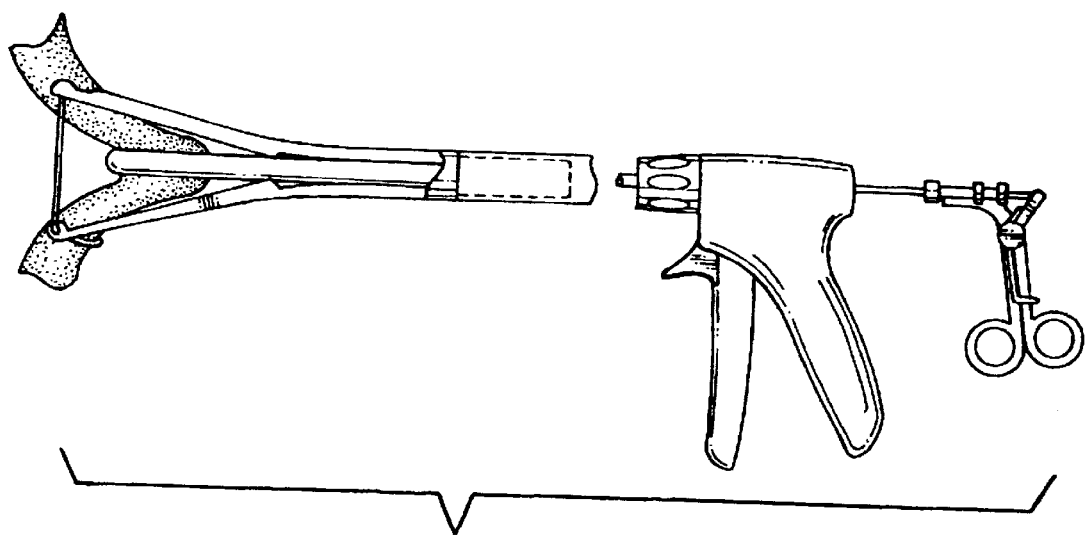
Figure 25G:
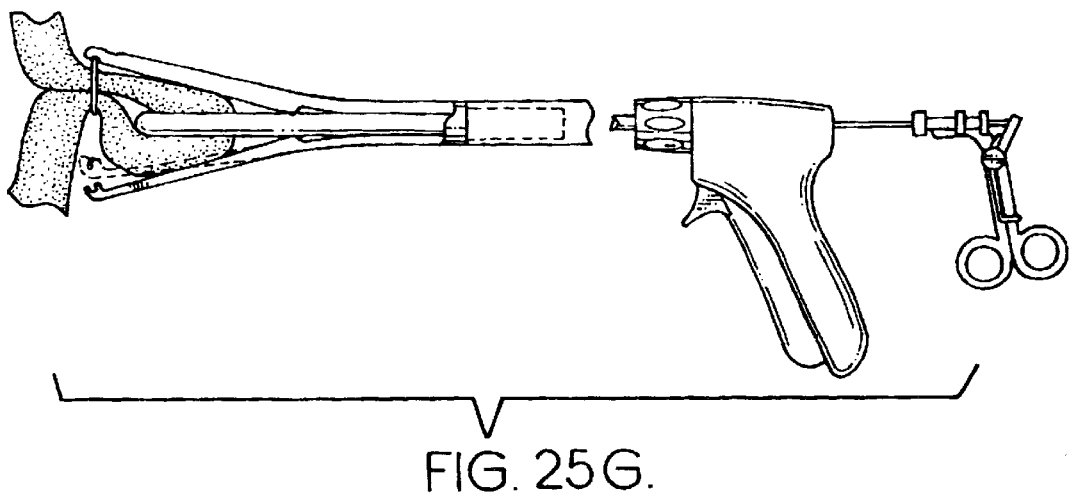
Figure 25H:
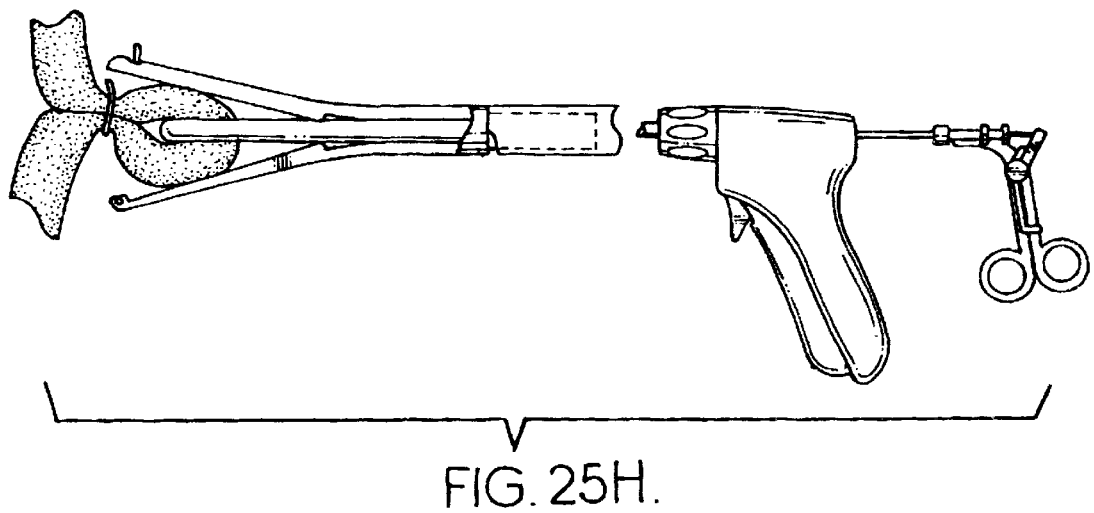
Figure 26A:
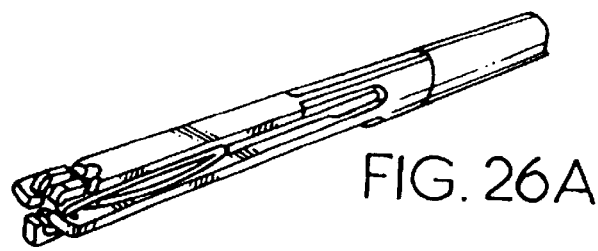
Figure 26B:
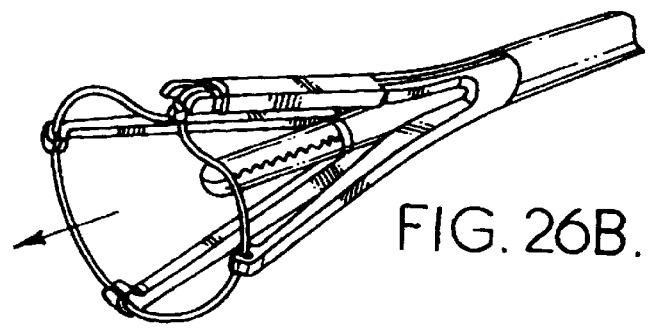
Figure 26C:
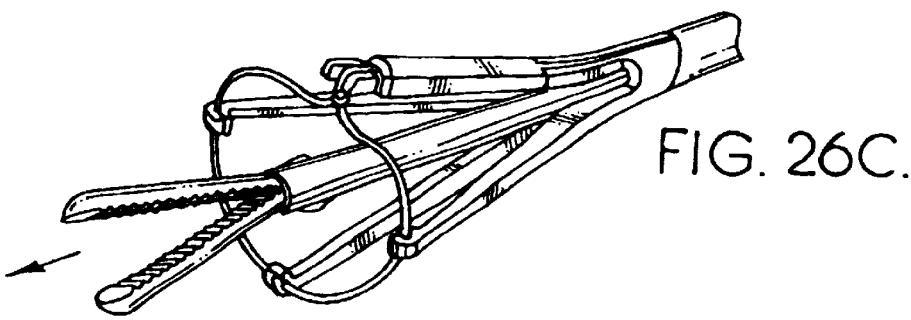
Figure 26G:
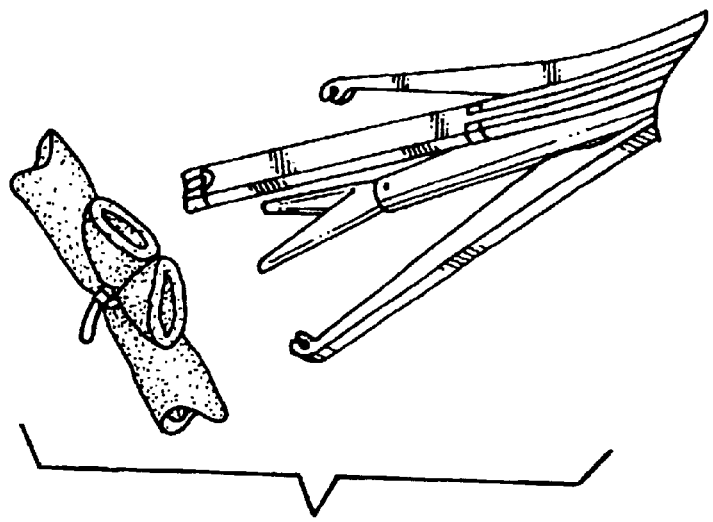

Operation of device 100 is indicated in FIGS. 25A–25H and 26A–26G. As can be understood from these figures as well as the above description, device 100 is inserted into a patient with the distal end thereof located adjacent to a target tissue, see, e.g., FIG. 26A. The device is operated to expand the suture loop 130 and a tissue grasper G, which is inserted through the proximal end of device 100, is used to grasp tissue and pull that tissue into the device, FIGS. 25A, 26B and 26C. Tissue grasper G includes an operating mechanism $185_G$ which is manipulated by a surgeon as indicated in FIGS. 25B and 25E. In the device discussed above, inserting the tissue grasper spreads the fingers into the open configuration. The elements of the device are operated to orient the tissue with respect to loop 130 so the tissue is encircled by the suture loop. Once the tissue is encircled, the device is operated to tighten the loop about the tissue and operate the cutter mechanism to cut the suture portion $130_1$ adjacent to slip knot $130_k$. Once the tissue is ligated with the suture loop, the grasping device is removed and endoscopic scissors are placed through the device to cut the tissue between the ligated loop as indicated in FIGS. 26F and 26G. If the surgeon desires, he can also take a sample of the tissue at this time by cutting off a portion and removing it with the grasper.

Figure 27A:
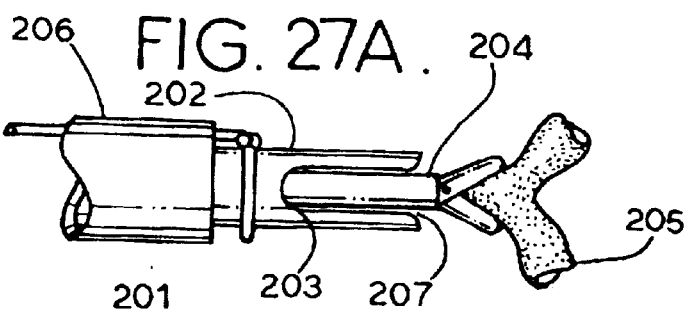
Figure 27C:
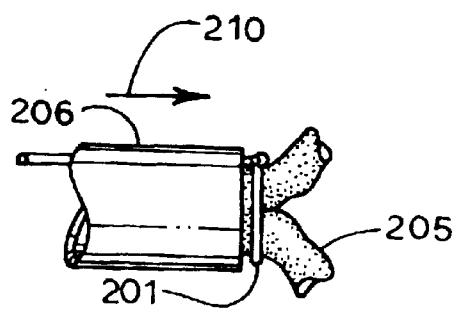
Figure 27B:
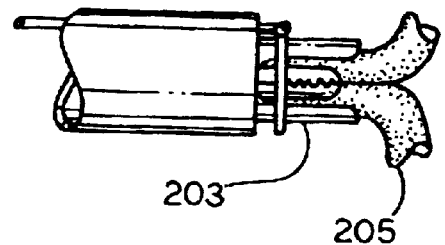

Yet another alternative form of the device is shown in FIGS. 27A–27F and in FIGS. 28A and 28B. FIG. 27A shows a suture loop 201 fixed on the outside surface 202 of a rigid body 203. A grasping device 204 is shown holding tissue 205 that will be ligated. Once the target tissue 205 is identified and stabilized, tissue 205 is placed within the suture loop 201. There are two methods for placing tissue 205 within suture loop 201. In the first method, rigid body 203 is stationary and grasping device 204 pulls tissue 205 into open lumen 207 of rigid body 203. The suture loop 201 is then pushed off the body 203 by means of a sliding tube 206 and is pushed onto tissue 205 to be ligated. A second method includes holding grasping device 204 stationary and moving rigid tube 203 towards the distal end of grasper 204. Once the tissue is within open lumen 207 of rigid tube 203, sliding tube 206 is deployed to push suture loop 201 off the rigid body 203 onto tissue 205. FIG. 27B shows tissue 205 within rigid body 203. FIG. 27C shows sliding tube 206 pushing in direction 210 to force suture loop 201 off rigid tube 203 onto tissue 205. Once suture loop 201 is at the desired location with respect to tissue 205, the surgeon will tighten loop 201 by operating the operating mechanism to pull the suture in direction 211 shown in FIG. 27D. Once the loop is tightened, as shown in FIG. 27E, cutter 208 is deployed to cut tail $201_t$ off suture loop 201. As shown in FIG. 27F, the trimmed suture loop 201' remains on tissue 205.

Yet another form of the suture loop controlling means is shown in FIGS. 28A and 28B. In the device 100' shown in FIGS. 28A and 28B, arms 220 are made from springy material such as nitenol, spring steel, or some other type of metal or plastic that has a material memory and attempts to return to an initial position after it has been deformed from that initial position. A plastic tip 225 is located at a distal tip of each arm 220 to hold the suture loop. Tips 225 can be molded or bonded to each arm. Arms 220 are biased toward the position shown in FIG. 28A, and are held in a collapsed position, shown in FIG. 28B, by being pulled into outer tube 221 when tube 221 is moved in direction 224 with respect to the arms. Once tube 221 is retracted in a direction opposite to direction 224 with respect to arms 220, the material memory of the arms causes them to move toward and into the FIG. 28A position and configuration. This deploys suture loop 223. It is noted that the suture loop is deployed independently of the tissue grasping device. Once suture loop 223 has been placed on the tissue, the outer tube is slid in direction 224 and arms 220 are contracted. Then, the device can be removed from the patient.

As mentioned above, there are many different ways to grasp tissue using an instrument that will fit down the ligating device. FIG. 29 shows a J-shaped tissue grasping element 308 in connection with the device shown in FIGS. 27A–27F.

FIGS. 30 and 31 show another device 100" for pushing the suture loop off the rigid body onto the tissue. Suture loop 330 is placed on the outside surface of rigid tube 331. Tail 333 extends through slider 332. Rigid tube 331 is not a completed closed shape as indicated in FIG. 31. While FIG. 31 indicates that the tube is circular in shape, it can be other shapes, including octagon, hexagon or other polygonal shape without departing from the scope of this invention. An internal lumen L is shown in FIG. 31. Slider 332 has a protrusion 334 on both sides thereof as shown in FIG. 31, which lock with mating slots 335 on rigid tube 331. Slider 332 is moved in direction 336 to push suture loop 330 off rigid tube 331. A cutter 336 is also housed in slider 332. Once suture loop 330 has been tightened around the tissue, cutter 336 is deployed to cut the tail of the suture adjacent to the slip knot as above discussed.

FIGS. 32–34 show various locations for a compliant member 340, 340' and 340" for accommodating different lengths of suture portion $130_1$ as discussed above. A compliant member can be positioned in a disposable cartridge 341, or in a handle 343 or in a shaft 342 as shown in FIGS. 32, 33 and 34 respectively. As discussed above, the function of the compliant member is to allow the same stroke at the trigger whether the instrument is fired on a large or a small tissue structure and to impart the same force on the loop to prevent formation of a loop which is overtight and which can cut the tissue or formation of a loop which is not tight enough and which can cause problems such as pregnancy in a tubal sterilization. When fired on a small tissue structure, the tail of the loop is pulled to a longer length. Conversely, when the device is fired on a large tissue, the tail of the suture loop is pulled to a shorter length. Therefore, a tolerance takeup mechanism is placed in the device. While a spring is shown for the compliant member, other forms can be used, such as an elastomeric bushing or the like.

Various means of attaching the cutter to the device can be used without departing from the scope of the invention. Examples of such means are shown in FIGS. 35–38. These various means can be dependent or independent of any deployment or tightening means. As shown in FIG. 35, cutter 350 is a manual linear cutter that is activated by the surgeon. Cutter 351 shown in FIG. 36 is a timed linear cutter that is attached to the tightening means and which cuts at a predetermined setting. The surgeon will have no input on when the suture is cut with the device 351 automatically activating. Cutter 352 shown in FIG. 37 is a manual rotational cutter. Upon rotation, a cam 353 on a rotation knob will make contact with the end of rod 354 thereby pushing the rod forward in direction 355 to cut the suture. A manual cutting sleeve 356 is shown in FIG. 38. The sleeve 356 has a sharp edge 357 on a cam surface 358 at the distal end of the device. Upon rotation, the cutter will be activated and will cut the suture.

As discussed above, the device of the present invention permits the surgical loop to be expanded between a first size and a second size in which one of those sizes is larger than the outer dimension of the main body whereby a wide range of tissue sizes can be accommodated, including tissues having sizes that are actually larger than the instrument itself. Several forms of such a device have already been discussed, including the forms shown in FIGS. 27A–27E where the loop rests on the outside surface of the device, and thus is larger than the outside dimension of the device. However, this disclosure is not intended to be limited by these exact forms. For example, as shown in FIGS. 39–43, other forms can also be used without departing from the scope of the present disclosure. As shown in FIG. 39, a device 400 includes a slidable ring 450 on the outside of a main body and is connected to fingers 451 through a stationary collar 452 by tensioning bands 453, such as elastomeric bands, metal wire, fiber or the like. When slidable ring 450 is moved proximally, by a trigger mechanism having a rod 400R, tension is applied to bands 453 which causes fingers 451 to pivot at a living hinge 454 outwardly in direction 400D. The fingers can be adjusted to an infinite size between a first and a second size with one of the sizes being shown in FIG. 39 as being larger than the outer dimension of the main body of device 400. Size adjustment of the fingers is effected by moving sliding ring 450 either proximally or distally as indicated in FIG. 40 by double-headed arrow 400M.

Yet another form of the device is shown in FIGS. 41–43 as device 470. Device 470 includes a suture loop 471 which is pushed off outer tube 472 once the target tissue and the device have been oriented relative to each other so the loop will encircle the tissue. As shown in FIG. 42, outer tube 472 includes two dovetail grooves 473 in which a top sliding element 474 and a bottom sliding element 475 are received. Sliding elements 474 and 475 are attached to a handle on the proximal end of the device. Suture tail 476 operates as discussed above. Operation of the sliding elements moves the suture loop 471 off of the main body of the device after the device and the tissue target have been oriented relative to each other so the loop will encircle the tissue.

As discussed above, since the device of the present invention can be used with a wide variety of tissue sizes, the tension applied to the suture loop must be controlled so that a loop associated with a large tissue will not receive too much tension and a loop associated with a small tissue will receive sufficient tension to accomplish the goals of properly ligating the tissue target. One system for adjusting the tension on the suture loop is shown in FIGS. 47–50 as device 490. One trigger actuates both the tensioning mechanism and the cutting mechanism in device 490. In device 490, the tensioning mechanism will pull the tail of the suture thereby causing the loop to constrict on the targeted tissue. When the desired amount of tension has been established on the loop, the cutting mechanism will be activated to cut the tail of the suture loop.

Device 490 is shown in the open condition in FIG. 47. A trigger 491 is fully open in this configuration. Trigger 491 is attached to a drive bar 492 which is attached to a tension coupler 493. Tension coupler 493 includes a proximal coupler part 494, a distal coupler part 495 and an elastic element such as a spring 496. The coupler parts are maintained together by a protrusion 497 on distal coupler part 495 that pops into a slot 498 on proximal coupler part 494. A suture drive bar 499 is attached to distal coupler part 495. Trigger 491 is shown in FIG. 48 as being activated in direction 500. Activation of trigger 491 in direction 500 forces drive bar 492 to push tension coupler 493 and suture drive bar 499 forward where suture drive bar 499 will push tail 501 of the suture loop. The proximal end of the suture tail is immobilized by anchor 502 so that tension is applied to the suture tail. Suture tail 501 is trained around a pivot 503 which thereby act as a pulley. With tension being applied to the suture tail 501, the diameter of the suture loop begins to decrease in direction 505. Once a set mount of resistance is met in the tension system, the tension coupler 493 begins to compress in direction 506 allowing uniform tightness on suture loop 504. This permits the same amount of tension on a large or small amount of tissue in the loop. The spring 496 is sized to get the proper amount of tension that is needed as the pre-set amount of tension. As shown in FIGS. 47–50, a protrusion 507 on the drive bar is nested in a slot 508 and the forward motion of the drive bar 492, indicated by arrow 510 in FIG. 50, caused by rotation of trigger 491 in direction 511 pushes cutter bar 509 in forward direction 510. This forward motion causes blade 512 of cutter bar 509 to cut suture tail 501. The distance 514 between the knot 513 of the suture loop 504 and the cut will remain the same on either a small or a large amount of tissue captured in the loop.

As discussed above, a slip knot is only one form of running element that can be used on the suture loop. Any element that will permit the loop to be tightened can be used, and two additional forms of the running element are shown in FIGS. 51 and 52. As shown in FIG. 51, a running element 520 includes an absorbable chuck 522 having a tortuous path 524 defined therethrough from one end 526 to the other end 528 and which receives suture tail 520T of loop 520S. A chock 530 is located in the chuck to contact the suture tail in a one-way manner. That is, the cock is angled to permit movement of the suture past the chock in direction 531 but not in direction 532. The tortuous path is self-cinching in that the suture can move in direction 531 but not in direction 532. Another form of the chuck is shown in FIG. 52 as chock 530' with a tortuous path 528' and a chock 530' on end 526'.

A molded chock will be smaller and more repeatable in tightening friction tan a knot in the size ranges of interest. Hand tied knots can be either too tight or too loose thus creating a possibility for non-repeatable characteristics in the instrument.

It is understood that while certain forms of the present invention have been illustrated and described herein, it is not to be limited to the specific forms or arrangements of parts described and shown.

What is claimed is:

1. A device for ligating tissue during an endoscopic procedure, comprising:
    an elongate main body having a proximal end and a distal end,
    an actuator positioned at said proximal end of said main body,
    a tissue manipulating instrument carried on said main body, said tissue manipulating instrument coupled to said actuator and movable by said actuator between a tissue engaging position and a tissue disengaging position,
    a suture including a loop coupled to a tail by a running element, said loop carried at said distal end of said main body and being tightenable around the tissue by pulling said tail when said tissue manipulating instrument is in said tissue engaging position, and
    a cutting device carried on said main body, said cutting device operating to cut said tail from said loop after said suture loop is tightened around the tissue by pulling said tail.

2. A method of endoscopic ligation of tissue using a unitary device including a tissue manipulating instrument and a suture including a loop coupled to a tail by a running element, said tissue manipulating instrument and suture loop each being carried on an elongate main body having proximal and distal ends, the method comprising:
    placing the distal end of the elongate main body through an incision to an internal operative site in the body of a patient,
    visualizing the internal operative site with an endoscope from externally of the internal operative site,
    engaging the tissue with the tissue manipulating instrument at the distal end of the main body,
    positioning the suture loop around the engaged tissue at the distal end of the main body while holding the suture loop at multiple distinct points on its circumference,
    tightening the suture loop around the engaged tissue by pulling the tail, and
    disengaging the tissue from the tissue manipulating instrument.

3. The method of claim 2, wherein:
    holding the suture loop at multiple distinct points further comprises using multiple fingers on a suture loop supporting unit, and
    tightening the suture loop further comprises moving the fingers radially inward toward one another to close the suture loop around the engaged tissue.

4. A device for ligating tissue during an endoscopic procedure, comprising:
    an elongate main body having a proximal end and a distal end,
    an actuator positioned at said proximal end of said main body,
    a tissue manipulating instrument carried on said main body, said tissue manipulating instrument coupled to said actuator and movable by said actuator between a tissue engaging position and a tissue disengaging position,
    a suture including a loop coupled to a tail by a running element, said loop carried at said distal end of said main body and being tightenable around the tissue by pulling said tail when said tissue manipulating instrument is in said tissue engaging position, and
    a plurality of fingers carried on said main body, said fingers engaging said suture loop at a plurality of distinct points and being movable to open and close said suture loop.

5. A device for ligating tissue during an endoscopic procedure, comprising:
    a) an instrument assembly having proximal and distal ends, and including
        1) an elongate main body,
        2) an actuator positioned at said proximal end,
        3) a tissue manipulating instrument carried on said main body, said tissue manipulating instrument coupled to said actuator and movable by said actuator between a tissue engaging position and a tissue disengaging position,
        4) a suture loop supporting unit positioned at the distal end,
    b) a suture including a loop coupled to a tail by a running element, said loop carried by said suture loop supporting unit such that said suture loop is in a position internal to the distal end of the assembly and said suture loop is tightenable around the tissue by pulling said tail when said tissue manipulating instrument is in said tissue engaging position.

6. The device of claim 5, further comprising:
    a cutting device carried on said main body, said cutting device operating to cut said tail from said suture loop after said suture loop is tightened around the tissue.

7. A method of endoscopic ligation of tissue using a unitary device including a tissue manipulating instrument and a suture including a loop coupled to a tail by a running element, said tissue manipulating instrument and said suture each being carried on an elongate main body having proximal and distal ends, the method comprising:
    placing the distal end of the elongate main body through an incision to an internal operative site in the body of a patient,
    visualizing the internal operative site with an endoscope from externally of the internal operative site, engaging the tissue with the tissue manipulating instrument at the distal end of the main body, carrying the suture loop by holding the suture loop at multiple distinct points on its circumference, positioning the suture loop around the engaged tissue at the distal end of the main body, tightening the suture loop around the engaged tissue by pulling the tail, and disengaging the tissue from the tissue manipulating instrument.

8. The method of claim 7, further comprising:

separating the tail from the tightened suture loop.

9. The method of claim 7, wherein:

carrying the suture loop further comprises using multiple fingers on a suture loop supporting unit, and tightening the suture loop further comprises moving the fingers radially inward toward one another to close the suture loop around the engaged tissue.

* * * * *